United States Patent
Williams et al.

(10) Patent No.: US 11,555,175 B2
(45) Date of Patent: Jan. 17, 2023

(54) CELL CULTURE METHODS AND MEDIA COMPRISING N-ACETYLCYSTEINE

(71) Applicant: Medimmune, LLC, Gaithersburg, MD (US)

(72) Inventors: Brena Williams, Gaithersburg, MD (US); Jeong Lee, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 16/679,713

(22) Filed: Nov. 11, 2019

(65) Prior Publication Data

US 2020/0208100 A1  Jul. 2, 2020

Related U.S. Application Data

(63) Continuation of application No. 15/318,798, filed as application No. PCT/US2015/036169 on Jun. 17, 2015, now abandoned.

(60) Provisional application No. 62/013,699, filed on Jun. 18, 2014.

(51) Int. Cl.
*C12N 5/00* (2006.01)
*C12P 21/02* (2006.01)
*C07K 16/00* (2006.01)
*C07K 16/24* (2006.01)

(52) U.S. Cl.
CPC ............ *C12N 5/0018* (2013.01); *C07K 16/00* (2013.01); *C07K 16/244* (2013.01); *C12P 21/02* (2013.01); *C07K 2317/14* (2013.01); *C12N 2500/32* (2013.01); *C12N 2500/34* (2013.01); *C12N 2500/36* (2013.01); *C12N 2500/44* (2013.01); *C12N 2501/999* (2013.01); *C12N 2511/00* (2013.01)

(58) Field of Classification Search
CPC .................................................. C12N 5/0018
See application file for complete search history.

(56) References Cited

U.S. PATENT DOCUMENTS

| | | | |
|---|---|---|---|
| 4,927,762 A | 5/1990 | Darfler | |
| 6,632,927 B2 | 10/2003 | Adair | |
| 7,332,303 B2 | 2/2008 | Schilling et al. | |
| 7,829,090 B2 | 11/2010 | Monk et al. | |
| 7,935,343 B2 | 5/2011 | Monk et al. | |
| 7,947,273 B2 | 5/2011 | Monk | |
| 9,315,575 B2 | 4/2016 | Monk et al. | |
| 9,856,317 B2 | 1/2018 | Monk et al. | |
| 10,793,827 B2 | 10/2020 | Barrett et al. | |
| 2004/0242495 A1 | 12/2004 | Staines et al. | |
| 2011/0262965 A1 | 10/2011 | Barrett et al. | |
| 2014/0134675 A1 | 5/2014 | Pla et al. | |

OTHER PUBLICATIONS

P. Isomaki et al., "Prolonged exposure of T cells to TNF downregulates TCR zeta and expression of the TCR/CD3 complex at the cell surface.", Journal of Immunology, vol. 166, No. 9, May 1, 2001, pp. 5495-5507.

Ping Zhou et al., "Changes in gene expression profiles of multiple myeloma cells induced by arsenic trioxide (ATO) possible mechanisms to explain ATO resistance in vivo", British Journal of Haematology, vol. 128, No. 5, Mar. 1, 2005, pp. 636-644.

Wang Wei et al., "Parthenolide-induced apoptosis in multiple myeloma cells involves reactive oxygen species generation and cell sensitivity depends on catalase activity", Apoptosis, London, GB, vol. 11, No. 12, Dec. 1, 2006 (Dec. 1, 2006), pp. 2225-2235.

Philippe J. Nadeau et al., "Modulation of CD40-activated B lymphocytes by N-acetylcysteine involves decreased phosphorylation of STAT3", Molecular Immunology, Pergamon, GB, vol. 49, No. 4, Oct. 17, 2011 (Oct. 17, 2011), pp. 582-592.

Estany et al: "Antioxidant activity of N-acetylcysteine, flavonoids and alpha-tocopherol on endometrial cells in culture", Journal of Reproductive Immunology, Elsevier Science Ireland LTD, IE, vol. 75, No. 1, Jul. 23, 2007 (Jul. 23, 2007), pp. 1-10.

Han Kyu Oh et al: "Effect of N-Acetylcystein on Butyrate-Treated Chinese Hamster Ovary Cells To Improve the Production of Recombinant Human Interferon-[beta]-1a", Biotechnology Progress, vol. 21, No. 4, Jan. 1, 2005 (Jan. 1, 2005), pp. 1154-1164.

Lederman et al. "A Single Amino Acid Substitution in a Common African Allele of the CD4 Molecule Ablates Binding of the Monoclonal Antibody, OKT4", Molecular Immunology, 1991. vol. 28, No. 11, pp. 1171-1181.

Li et al., "Temporal associations between interleukin 22 and the extracellular domains of IL-22R and IL-IOR2", International Immunopharmacology, vol. 4, pp. 693-708, 2004.

Panka et al., "Variable Region Framework Differences Result in Decreased or Increased Affinity of Variant Anti-Digoxin Antibodies", Proc. Natl. Acad. Sci. USA vol. 85, pp. 3080-3084 (May 1988).

Rudikoff et al.. "Single Amino Acid Substitution Altering Antigen-Binding Specificity", Proc. Natl. Acad. Sci. USA vol. 79, pp. 1979-1983 (Mar. 1982).

Amit et al . . . "Three-Dimensional Structure of an Antigen-Antibody Complex at 2.8 A Resolution", Science, Vot. 233, pp. 747-753, (Aug. 1986).

*Primary Examiner* — Prema M Mertz

(57) ABSTRACT

This application provides improved cell culture media and cell culture methods comprising N-acetylcysteine. These improved cell culture media and cell culture methods increase cell viability, cellular growth rate and/or reduce cell doubling time of cholesterol auxotrophic cells, myeloma cells, and hybridoma cells.

6 Claims, 12 Drawing Sheets

Specification includes a Sequence Listing.

```
SEQUENCE LISTING

<160> NUMBER OF SEQ ID NOS: 32

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Trp Ile Ser Ala Asn Asn Gly Asp Thr Asn Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80
```

```
Asp Glu Ala Asp Tyr Tyr Cys Gln Val Trp Asp Thr Gly Ser Asp Pro
            85                  90                  95

Val Val Phe Gly Gly Gly Thr Lys Leu Thr Val Leu
            100                 105

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Tyr Gly Leu Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Ile Ser Ala Asn Asn Gly Asp Thr Asn Tyr Gly Gln Glu Phe Gln
1               5                   10                  15

Gly

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ser Ser Ser Ser Trp Ala Arg Trp Phe Phe Asp Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Asn Ile Ile Gly Ser Lys Leu Val His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Asp Gly Asp Arg Pro Ser
1               5
```

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Gln Val Trp Asp Thr Gly Ser Asp Pro Val Val
1               5                   10

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Asn Tyr
            20                  25                  30

Gly Leu Ser Trp Val Arg Gln Ala Pro Gly Gln Gly Leu Glu Trp Met
        35                  40                  45

Gly Trp Ile Ser Ala Asn Asn Gly Asp Thr Asn Tyr Gly Gln Glu Phe
    50                  55                  60

Gln Gly Arg Ile Thr Met Thr Thr Glu Thr Ser Thr Asn Thr Ala His
65                  70                  75                  80

Met Glu Leu Arg Ser Leu Arg Ser Asp Asp Thr Ala Val Tyr Tyr Cys
                85                  90                  95

Val Arg Asp Ser Ser Ser Asn Trp Ala Arg Trp Phe Phe Asp Leu Trp
            100                 105                 110

Gly Lys Gly Thr Met Val Thr Val Ser Ser
        115                 120

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Ser Tyr Val Leu Thr Gln Pro Pro Ser Val Ser Val Ala Pro Gly Gln
1               5                   10                  15

Thr Ala Arg Ile Pro Cys Gly Gly Asn Asn Ile Gly Ser Lys Leu Val
            20                  25                  30

His Trp Tyr Gln Gln Lys Pro Gly Gln Ala Pro Val Leu Val Val Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Ile Asp Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Tyr Gly Leu Ser
1               5

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Ile Ser Ala Asn Asn Gly Asp Thr Asn Tyr Gly Gln Glu Phe Gln
1               5                   10                  15

Gly

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ser Ser Ser Asn Trp Ala Arg Trp Phe Phe Asp Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Asn Asn Ile Gly Ser Lys Leu Val His
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Asp Gly Asp Arg Pro Ser
1               5

<210> SEQ ID NO 16
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 16

Gln Val Trp Asp Thr Gly Ser Asp Pro Val Val
1               5                   10

<210> SEQ ID NO 17
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Trp Ile Asn Tyr Asp Gly Asn Thr Gln Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 18
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
            100                 105

<210> SEQ ID NO 19
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Tyr Gly Leu Ser
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Ile Asn Tyr Asp Gly Gly Asn Thr Gln Tyr Gly Gln Glu Phe Gln
1               5                   10                  15

Gly

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Ser Ser Ser Ser Trp Ala Arg Trp Phe Phe Asp Leu
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Asn Ile Ile Gly Ser Lys Leu Val His
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Asp Gly Asp Arg Pro Ser
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Gln Val Trp Asp Thr Gly Ser Asp Pro Val Val
1               5                   10

<210> SEQ ID NO 25
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Gln Thr
            20                  25                  30

Gly Val Ser Trp Val Arg Gln Ala Pro Gly Gln Gly Leu Glu Trp Met
        35                  40                  45

Gly Trp Ile Ser Ala Asn Asn Gly Asp Thr Asn Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Ser Ser Ser Ser Trp Ala Arg Trp Phe Phe Asp Leu Trp
            100                 105                 110

Gly Arg Gly Thr Leu Val Thr Val Ser Ser
            115                 120

<210> SEQ ID NO 26
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

His Trp Tyr Gln Gln Lys Pro Gly Gln Ala Pro Val Leu Val Ile Tyr
        35                  40                  45

Asp Asp Gly Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Gly Ser Asp Pro
                85                  90                  95

Val Val Phe Gly Gly Gly Thr Lys Leu Thr Val Leu
            100                 105

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 27

Gln Thr Gly Val Ser
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Ile Ser Ala Asn Asn Gly Asp Thr Asn Tyr Gly Gln Glu Phe Gln
1               5                   10                  15

Gly

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Ser Ser Ser Ser Trp Ala Arg Trp Phe Phe Asp Leu
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Asn Ile Ile Gly Ser Lys Leu Val His
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Asp Gly Asp Arg Pro Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Val Trp Asp Thr Gly Ser Asp Pro Val Val
1               5                   10

CELL CULTURE METHODS AND MEDIA COMPRISING N-ACETYLCYSTEINE

REFERENCE TO SEQUENCE LISTING SUBMITTED ELECTRONICALLY

The content of the electronically submitted sequence listing in ASCII text file (Name: IL13-310P1_SL.txt; Size: 15,073 bytes; and Date of Creation: Jun. 11, 2014) filed with the application is incorporated herein by reference in its entirety.

BACKGROUND

Many important protein-based biologic therapeutics are produced in cell culture. These include, but are not limited to, both recombinant proteins and antibody therapeutics. Producing biologic therapeutics in cell culture increases the cost of manufacturing both commercial products and clinical candidates as compared to traditional small-molecule therapeutics. One of the significant limiting factors is the time it takes to scale up a production run in a manufacturing facility from a frozen stock of cells, as well as, high plant occupancy and utilization rates which result from the relatively slow growth of cells used to produce recombinant proteins and antibody therapeutics. As a result, there is a need to develop optimized cell culture methods and reagents which increase cell viability and/or cell growth rates (resulting in reduced cell doubling time) to reduce production scale-up timelines, plant occupancy or utilization rates, and reduce costs. Serum or other animal-protein ingredients are often used to enhance the ability of cells to grow in a laboratory setting. However, due to regulatory or potential safety concerns, cell culture media and reagents often do not contain serum or other animal-protein ingredients when manufacturing biologic therapeutics. Removal of animal-protein components makes it more difficult for cells to grow in culture and more difficult for cells to thaw and start growing from a frozen stock, thereby reducing product yields and increasing plant occupancy, utilization rates, and costs. Therefore, precisely when production efficiency becomes most important, cell culture medium ingredients are restricted. Thus, the art faces challenges in optimizing cell culture ingredients for cell lines used to produce protein-based biologic therapeutics such as heterologous proteins and antibody therapeutics. Indeed, the involvement of large number of media components, the complexity of cellular metabolic pathways and the interdependence between the various media components and complex cellular pathways, often makes it is very difficult to optimize cell culture reagents or methods. Against this backdrop, provided herein are cell culture media and cell culture methods comprising N-acetylcysteine (NAC), which when added to cell culture media and/or used in cell culture methods involving a cholesterol auxotroph, a myeloma, or a hybridoma surprisingly increases cell viability, cellular growth rate and reduces cell doubling time.

Others have suggested adding N-acetyl cysteine to cell culture media as a generic amino acid source (see, e.g., EP 2351827; at amounts orders of magnitude lower than used herein) or as a generic reducing agent (see, e.g., EP1434856, WO2012095731, US20060258003) to support the growth of T cells, neuronal progenitor/stem cells, or muscle progenitor/stems cells, respectively. In contrast, provided herein are cell culture media and cell culture methods comprising N-acetylcysteine that increase cell viability, cellular growth rate and reduce cell doubling time of cholesterol auxotrophs, myeloma, or hybridoma cells. As described herein (see, e.g. Examples 1-6) N-acetylcysteine, when added to cell culture media already containing amino acids and reducing agents, surprisingly increased cell viability, cellular growth rate, and reduced cell doubling time of NS0 cells.

SUMMARY

The specification and claims provide a variety of cell culture media and methods comprising N-acetylcysteine (NAC), with the following providing a summary of some of those media and methods. In accordance with the description, one embodiment provides a cell culture method comprising: (a) providing a cell culture medium sufficient to support cell growth, wherein the cell culture medium comprises N-acetylcysteine; and (b) culturing a cell in the cell culture medium, wherein the cell is a cholesterol auxotroph, a myeloma, or a hybridoma. In another embodiment, a method of increasing cell viability comprises: (a) providing a cell culture medium sufficient to support cell growth, wherein the cell culture medium comprises N-acetylcysteine; and (b) culturing a cell in the cell culture medium, wherein the cell is a cholesterol auxotroph, a myeloma, or a hybridoma. In a further aspect, a method of increasing cell growth rate comprises: (a) providing a cell culture medium sufficient to support cell growth, wherein the cell culture medium comprises N-acetylcysteine; and (b) culturing a cell in the cell culture medium, wherein the cell is a cholesterol auxotroph, a myeloma, or a hybridoma. In another embodiment, a method of reducing cell doubling time comprises: (a) providing a cell culture medium sufficient to support cell growth, wherein the cell culture medium comprises N-acetylcysteine; and (b) culturing a cell in the cell culture medium, wherein the cell is a cholesterol auxotroph, a myeloma, or a hybridoma. In one embodiment of the methods disclosed herein, the cell is a cholesterol auxotroph. In another embodiment of the methods disclosed herein, the cell is a myeloma. In a further embodiment of the methods disclosed herein the cell is a hybridoma.

In one embodiment, the cells are being thawed from a frozen stock. In another embodiment, the cells are in an expansion phase. In another embodiment, the cell culture medium is a serum free and animal-protein free medium. In another embodiment, the cell culture medium is a chemically-defined medium. In another embodiment, the medium comprises lipids.

In another embodiment, the cells are derived from a mammal. In another embodiment, the mammalian cells are murine, hamster, rat, monkey, or human. In another embodiment, the cells are cholesterol auxotrophs. In one embodiment, a cholesterol auxotroph may comprise NS0, NS1, U937, M19, SRD-12B, SRD-13A, CHO-215, X63 cells, cell lines derived from these cells lines, or any other cell engineered to be a cholesterol auxotroph. In another embodiment, the cells are NS0 cells. In another embodiment, the cells are a myeloma or a hybridoma.

In another aspect a cell culture medium comprises N-acetylcysteine, a carbohydrate source, an amino acid source, and a cholesterol source. In another embodiment, the carbohydrate source and the amino acid source are different. In another embodiment, the medium further comprises lipids. In another embodiment, the cell culture medium comprises a carbohydrate source, an amino acid source, a cholesterol source, vitamins, inorganic salts, trace metals, surfactants, and a pH buffer.

In another embodiment, the cell culture medium comprises N-acetylcysteine at a concentration of from about 0.25 mM to about 3 mM. In another embodiment, the cell culture medium comprises N-acetylcysteine at a concentration of from about 0.5 to about 2.5 mM. In another embodiment, the cell culture medium comprises N-acetylcysteine at a concentration of from about 1.0 to about 1.5 mM. In another embodiment, the cell culture medium comprises N-acetylcysteine at a concentration of about 1 mM. In another embodiment, the cell culture medium comprises N-acetylcysteine at a concentration of about 1.5 mM. In another embodiment, the cell culture medium comprises N-acetylcysteine at a concentration of at least about 0.5 mM, at least about 1.0 mM, at least about 1.5 mM or at least about 2.0 mM. In another embodiment, the cell culture medium comprises yeastolate. In another embodiment, the cell culture medium comprises 1 g/L of yeastolate.

In another embodiment, the average doubling time is shorter than in a cell culture with a control medium excluding N-acetylcysteine. In another embodiment, the average doubling time is reduced by at least 10% compared to a cell culture medium without N-acetylcysteine. In another embodiment, the average doubling time is reduced by at least 15% compared to a cell culture medium without N-acetylcysteine. In another embodiment, the average doubling time is reduced by at least 20% compared to a cell culture medium without N-acetylcysteine. In another embodiment, the average doubling time is reduced by at least 25% compared to a cell culture medium without N-acetylcysteine. In another embodiment, the average doubling time is reduced by at least 50% compared to a cell culture medium without N-acetylcysteine. In another embodiment, the average doubling time is 60 hours or less in a cell culture medium containing N-acetylcysteine. In another embodiment, the average doubling time is 42 hours or less in a cell culture medium containing N-acetylcysteine. In another embodiment, the average doubling time is 34 hours or less in a cell culture medium containing N-acetylcysteine. In another embodiment, the average doubling time is 30 hours or less in a cell culture medium containing N-acetylcysteine. In another embodiment, the average doubling time is 29 hours or less in a cell culture medium containing N-acetylcysteine.

In another embodiment, the cell viability is increased over a cell culture with a control medium excluding N-acetylcysteine. In another embodiment, the cell viability is increased by at least 5% compared to a cell culture medium without N-acetylcysteine. In another embodiment, the cell viability is increased by at least 7% compared to a cell culture medium without N-acetylcysteine. In another embodiment, the cell viability is increased by at least 10% compared to a cell culture medium without N-acetylcysteine. In another embodiment, the cell viability is at least 90%. In another embodiment, the cell viability is at least 92%. In another embodiment, the cell viability is at least 93%.

In another embodiment, the cells do not express a heterologous protein. In another embodiment, the cells express a heterologous protein. In another embodiment, the cells are transformed with a heterologous nucleic acid. In another embodiment, the heterologous nucleic acid is cDNA, a vector, a plasmid, a nucleic acid operably linked to a promoter, and/or nucleic acid that incorporates into the genome. In another embodiment, the heterologous protein is transiently expressed. In another embodiment, the heterologous protein is stably expressed. In another embodiment, the heterologous protein is an antibody or antigen-binding fragment thereof. In another embodiment, the antibody or antigen-binding fragment thereof is an IL-13 antibody. In another embodiment, the antibody is BAK502G9 (as represented by the VH and VL domains of SEQ ID NOs 1-2 and/or the heavy and light chain CDRs of SEQ ID NOs 3-8), BAK278D6 (as represented by the VH and VL domains of SEQ ID NOs 9-10 and/or the heavy and light chain CDRs of SEQ ID NOs 11-16), BAK1183H4 (as represented by the VH and VL domains of SEQ ID NOs 17-18 and/or the heavy and light chain CDRs of SEQ ID NOs 19-24), or BAK1167F2 (as represented by the VH and VL domains of SEQ ID NOs 25-26 and/or the heavy and light chain CDRs of SEQ ID NOs 27-32).

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

DESCRIPTION OF THE SEQUENCES

Figure 1:
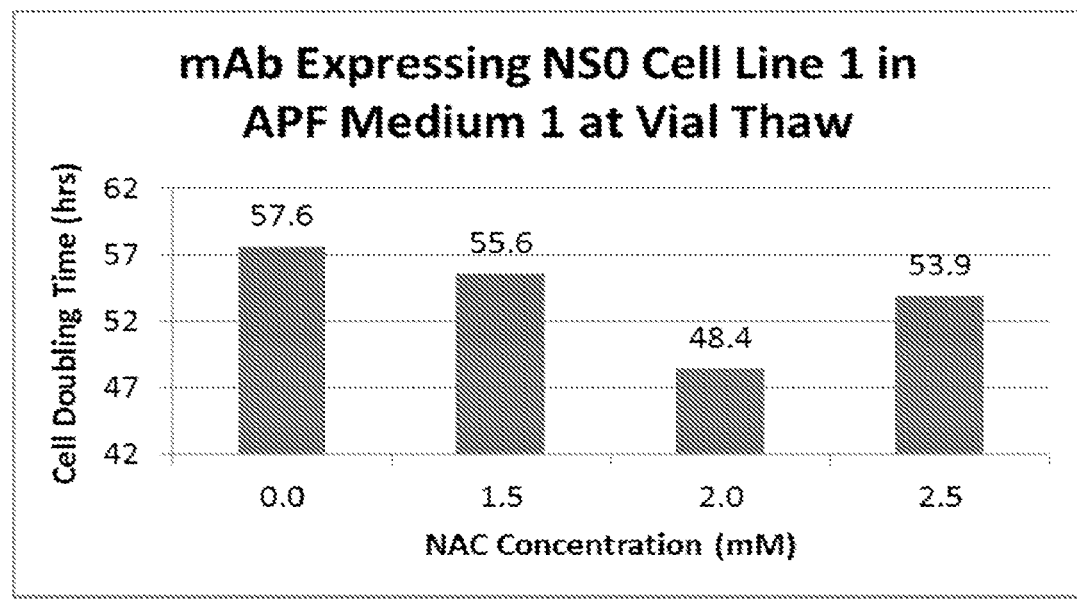
FIG. 1 shows population doubling time of NS0 Cell Line 1 expressing a monoclonal antibody ("mAb") against IL-9 in animal-protein free (APF) medium 1 at vial thaw. Frozen NS0 Cell Line 1 cells thawed in animal-protein free (APF) medium 1 were supplemented with N-acetylcysteine (NAC) (1.5 mM, 2.0 mM, or 2.5 mM) and viable cell density during exponential growth phase was used to calculate average doubling time. Addition of 1.5 mM to 2.5 mM NAC improved cell viability, increased cell growth and reduced average cell doubling time from vial thaw of NS0 Cell Line 1. hrs=hours; mM=millimolar.

Table 1 provides a listing of certain sequences referenced in present embodiments.

TABLE 1

| Description | Sequence | SEQ ID NO |
|---|---|---|
| BAK502G9 VH | QVQLVQSGAEVKKPGASVKVSCKASGYTFT<u>NYGL SWV</u>RQAPGQGLEWMG<u>WISANNGDTNYGQEFQG</u>RV TMTTDTSTSTAYMELRSLRSDDTAVYYCAR<u>DSSS SWARWFFDL</u>WGRGTLVTVSS | 1 |
| BAK502G9 VL | SYVLTQPPSVSVAPGKTARITC<u>GGNIIGSKLVH</u>W YQQKPGQAPVLVIY<u>DDGDRPS</u>GIPERFSGSNSGN TATLTISRVEAGDEADYYC<u>QVWDTGSDPVV</u>FGGG TKLTVL | 2 |
| BAK502G9 HC CDR1 | NYGLS | 3 |
| BAK502G9 HC CDR2 | WISANNGDTNYGQEFQG | 4 |
| BAK502G9 HC CDR3 | DSSSSWARWFFDL | 5 |
| BAK502G9 LC CDR1 | GGNIIGSKLVH | 6 |
| BAK502G9 LC CDR2 | DDGDRPS | 7 |
| BAK502G9 LC CDR3 | QVWDTGSDPVV | 8 |

TABLE 1-continued

| Description | Sequence | SEQ ID NO |
|---|---|---|
| BAK278D6 VH | EVQLVQSGAEVKKPGASVKVSCKASGYTFRNYGL SWVRQAPGQGLEWMGWISANNGDTNYGQEFQGRI TMTTETSTNTAHMELRSLRSDDTAVYYCVRDSSS NWARWFFDLWGKGTMVTVSS | 9 |
| BAK278D6 VL | SYVLTQPPSVSVAPGQTARIPCGGNNIGSKLVHW YQQKPGQAPVLVVYDDGDRPSGIPERFSGSNSGN TATLTISRIDAGDEADYYCQVWDTGSDPVVFGGG TKLTVL | 10 |
| BAK278D6 HC CDR1 | NYGLS | 11 |
| BAK278D6 HC CDR2 | WISANNGDTNYGQEFQG | 12 |
| BAK278D6 HC CDR3 | DSSSNWARWFFDL | 13 |
| BAK278D6 LC CDR1 | GGNNIGSKLVH | 14 |
| BAK278D6 LC CDR2 | DDGDRPS | 15 |
| BAK278D6 LC CDR3 | QVWDTGSDPVV | 16 |
| BAK1183H4 VH | QVQLVQSGAEVKKPGASVKVSCKASGYTFTNYGL SWVRQAPGQGLEWMGWINYDGGNTQYGQEFQGRV TMTTDTSTSTAYMELRSLRSDDTAVYYCARDSSS SWARWFFDLWGRGTLVTVSS | 17 |
| BAK1183H4 VL | SYVLTQPPSVSVAPGKTARITCGGNIIGSKLVHW YQQKPGQAPVLVIYDDGDRPSGIPERFSGSNSGN TATLTISRVEAGDEADYYCQVWDTGSDPVVFGGG TKLTVL | 18 |
| BAK1183H4 HC CDR1 | NYGLS | 19 |
| BAK1183H4 HC CDR2 | WINYDGGNTQYGQEFQG | 20 |
| BAK1183H4 HC CDR3 | DSSSSWARWFFDL | 21 |
| BAK1183H4 LC CDR1 | GGNIIGSKLVH | 22 |
| BAK1183H4 LC CDR2 | DDGDRPS | 23 |
| BAK1183H4 LC CDR3 | QVWDTGSDPVV | 24 |
| BAK1167F2 VH | QVQLVQSGAEVKKPGASVKVSCKASGYTFEQTGV SWVRQAPGQGLEWMGWISANNGDTNYGQEFQGRV TMTTDTSTSTAYMELRSLRSDDTAVYYCARDSSS SWARWFFDLWGRGTLVTVSS | 25 |
| BAK1167F2 VL | SYVLTQPPSVSVAPGKTARITCGGNIIGSKLVHW YQQKPGQAPVLVIYDDGDRPSGIPERFSGSNSGN TATLTISRVEAGDEADYYCQVWDTGSDPVVFGGG TKLTVL | 26 |
| BAK1167F2 HC CDR1 | QTGVS | 27 |
| BAK1167F2 HC CDR2 | WISANNGDTNYGQEFQG | 28 |
| BAK1167F2 HC CDR3 | DSSSSWARWFFDL | 29 |
| BAK1167F2 LC CDR1 | GGNIIGSKLVH | 30 |
| BAK1167F2 LC CDR2 | DDGDRPS | 31 |
| BAK1167F2 LC CDR3 | QVWDTGSDPVV | 32 |

DEFINITIONS

In order that the present disclosure can be more readily understood, certain terms are first defined. Additional definitions are set forth throughout the detailed description.

In this specification and the appended claims, the singular forms "a", "an" and "the" include plural referents unless the context clearly dictates otherwise. The terms "a" (or "an"), as well as the terms "one or more," and "at least one" can be used interchangeably herein. For example, a cell may refer to a single cell or a population of cells.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" or "approximately" as used in connection with a numerical value throughout the specification and the claims denotes an interval of accuracy, familiar and acceptable to a person skilled in the art. In general, such interval of accuracy is ±5%.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "N-acetylcysteine", "N-acetyl-cysteine", "N-acetyl-L-cysteine", or "Acetylcysteine" (abbreviated "NAC") refers to a compound derived from cysteine having an acetyl group attached to the nitrogen atom. N-acetylcysteine is also referred to as (2R)-2-acetamido-3-sulfanylpropanoic acid (IUPAC) and has a Chemical Abstracts Service (CAS) Registry Number of 616-91-1. N-acetylcysteine is available from various commercial vendors including Sigma-Aldrich.

As used herein, the term "cholesterol auxotroph" refers to a cell or cell line that requires cholesterol for growth but is unable to synthesize it. Exemplary cholesterol auxotroph include, but are not limited to, NS0, NS1, U937, M19, SRD-12B, SRD-13A, CHO-215, X63 cells, cell lines derived from these cells lines, or any other cell engineered to be a cholesterol auxotroph. Methods of identifying and/or culturing cholesterol auxotrophs are well known in the art. See, e.g., Keen et al., Cytotechnology. 17(3):203-11 (1995); Gorfien et al., Biotechnol Prog. 16(5):682-7 (2000); Fu, et al., Proc Natl Acad Sci USA. 102(41):14551-6 (2005); Birch et al., Adv Drug Delivery Rev. 58:671-685 (2006); Feng et al., MAbs. 2(5): 466-477 (2010), each herein incorporated by reference in its entirety.

As used herein, the terms "myeloma" and "myeloma cells" refer to an immortalized cell line derived from bone marrow cells such as myelocytes, plasma cells or B cells. Exemplary myeloma cells include, but are not limited to, X63Ag8, Sp2/0, NS1, NS0, J558L, U266, U937, P3U1, XG-1, XG-2, XG-3, XG-4, XG-5, XG-6, XG-7, XG-8, XG-9, U266, RPM1-8226, LP1, L363, OPM1, OPM2, and NCLH929 cells or cell lines derived from these cells lines. Methods of identifying and/or culturing myeloma cells are well known in the art. See, e.g., Fuller, et al. Preparation of Myeloma Cells. Current Protocols in Molecular Biology. 18:11.5.1-11.5.3 (2001); Zhang et al., Blood, 83(12):3654-3663 (1994); and Tai et al., J. Immunol. Methods. 235:11-19 (2000), each herein incorporated by reference in its entirety.

As used herein, the terms "hybridoma" and "hybridoma cells" refer to an immortalized cell line formed by fusing a B cell with an immortalized cell (e.g. a myeloma cell). Methods of generating and/or culturing hybridomas are well known in the art. See, e.g., Kohler and Milstein, Nature 256:495 (1975); Galfrè and Milstein. Methods Enzymol. 73(Pt B):3-46 (1981); and Goding, Monoclonal Antibodies: Principles and Practice, Academic Press (1986), each herein incorporated by reference in its entirety.

As used herein, the term "cell culture medium" refers to a liquid or substrate designed to support the growth of cells derived from multi-cellular eukaryotes, especially animal cells. Exemplary cell culture media and methods of culturing cells are described in Doyle et al., "Mammalian cell culture: essential techniques" Wiley, (1997); Freshney, "Culture of Animal Cells: A Manual of Basic Technique and Specialized Applications" John Wiley & Sons, (2011); and Meenakshi, "Cell Culture Media: A Review" Mater Methods. 3:175 (2013) each herein incorporated by reference in its entirety.

As used herein, the term "serum free medium" refers to a cell culture medium that does not contain animal serum such as fetal bovine serum, bovine serum albumin or human serum albumin. As used herein, the term "animal-protein free medium" refers to a cell culture medium that does not contain proteins and/or protein components from higher multicellular non-plant eukaryotes such as albumin, transferrin, insulin or growth factors. Animal proteins and protein components are to be distinguished from non-animal proteins, small peptides and oligopeptides obtainable from plants (usually 10-30 amino acids in length) or lower eukaryotes, such as yeast, which may be included into the animal-protein free cell culture medium according to the invention. Serum free and animal-protein free medium according to the methods disclosed herein may be based on any basal medium such as DMEM, Ham's F12, Medium 199, McCoy or RPMI generally known to the skilled worker. The basal medium may comprise a number of ingredients, including amino acids, vitamins, organic and inorganic salts, and sources of carbohydrate, each ingredient being present in an amount which supports the cultivation of a cell which is generally known to the person skilled in the art. The medium may contain auxiliary substances, such as buffer substances like sodium bicarbonate, antioxidants, stabilizers to counteract mechanical stress, or protease inhibitors. If required, a non-ionic surfactant such as mixtures of polyethylene glycols and polypropylene glycols (e.g. Pluronic F68®, SERVA) can be added as a defoaming agent. Examples of serum free and animal-protein free medium are well known in the art as described in Mariani et al., "Commercial serum-free media: hybridoma growth and monoclonal antibody production." J Immunol Methods. 145:175-83 (1991); Barnes et al., "Methods for growth of cultured cells in serum-free medium." Anal Biochem. 102: 255-70 (1980); Waymouth, "Preparation and use of serum-free culture media." In: Barnes D W, Sirbasku D A, Sato G H, editors. "Methods for preparation of media, supplements and substrata for serum-free animal cell culture." New York: Liss; (1984); and Mendelson et al., "Culture of human lymphocytes in serum-free medium." In: Barnes D W, Sirbasku D A, Sato G H, editors. "Methods for serum-free culture of neuronal and lymphoid cells." New York: Liss; (1984) each herein incorporated by reference in its entirety.

As used herein, the term "chemically-defined medium" is a cell growth medium suitable for the cell culture of human or animal cells in which all of the chemical components are known.

As used herein, a "cell culture medium sufficient to support cell growth" refers to a cell culture medium capable of supporting the growth, survival and/or proliferation of a cell. In general, a "cell culture medium sufficient to support cell growth" comprises an appropriate energy source and a complement of amino acids, vitamins, salts, and/or nutrients generally known to the skilled person. Exemplary cell culture media sufficient to support cell growth include commercially available media, chemically-defined media, serum-free medium, and animal-protein free media, as generally known to the skilled worker.

As used herein, the term "cell viability" refers to the ability of a cell to live or develop. In general, determining "cell viability' requires measuring the ability of a cell or cell population to live or develop (including, e.g., making a determination of the number of living or dead cells, based on a total cell sample), as generally known to the skilled worker. Cell viability assays are well known in the art and include: cytolysis or membrane leakage assays (e.g. using Propidium iodide, Trypan blue and/or 7-Aminoactinomycin D), Mitochondrial activity or caspase assays (e.g. using Resazurin and/or Formazan), cell functional assays (e.g. motility assays, cell proliferation or growth assays), Genomic and/or proteomic assays (e.g. measuring the expression of various genes or proteins associated with cell death, damage or stress), Cytotoxicity assays, and vital staining. See Chapter 15, "Assays for Cell Viability, Proliferation and Function" In: "The Molecular Probes Handbook. A Guide to Fluorescent Probes and Labeling Technologies" (I. Johnson and M. Spence (eds.) 11th Edition, Life Technologies (2010) herein incorporated by reference in its entirety.

As used herein, the term "cell doubling time" or "doubling time" refers to the period of time required for a cell or population of cells to double in number. The doubling time of a cell or cell population can be determined using the following formula: DT=T ln2/ln(X2/X1), where DT=doubling time; T is the incubation time in any units; X1 is the cell number at the beginning of the incubation time; and X2 is the cell number at the end of the incubation time. As used herein, cell doubling time is measured when the relative growth rate of a cell or cell population is constant (e.g. in the exponential growth or log phase). Cell counting assays are well known in the art and include counting cells; using a counting chamber (e.g. a hemocytometer); using a spectrophotometer; using a Coulter counter; using Flow cytometry; or using microscopy. See Chapter 15, "Assays for Cell Viability, Proliferation and Function" In: "The Molecular Probes Handbook. A Guide to Fluorescent Probes and Labeling Technologies" (I. Johnson and M. Spence (eds.) 11th Edition, Life Technologies (2010) herein incorporated by reference in its entirety.

As used herein, the term "heterologous nucleic acid" refers to a nucleic acid molecule (e.g. a polynucleotide, cDNA, DNA, RNA, or fragment thereof) introduced into a cell using standard recombinant DNA and molecular cloning techniques including, but not limited to, those described in Sambrook et al., "Molecular Cloning: A Laboratory Manual" Second Edition, Cold Spring Harbor Laboratory Press, Cold Spring Harbor, N.Y. (1989); Silhavy et al., "Experiments with Gene Fusions" Cold Spring Harbor Laboratory Press, Cold Spring Harbor, N.Y. (1984); and Ausubel, F. M. et al., "Current Protocols in Molecular Biology" published by Greene Publishing Assoc. and Wiley-Interscience (1987) each herein incorporate by reference in their entireties. Nucleic acids according to the present invention may comprise DNA or RNA and may be wholly or partially synthetic.

As used herein the term "transformation" or "transformed" refers to the transfer of a nucleic acid molecule or fragment thereof into a host cell, resulting in inheritance of the nucleic acid molecule or fragment thereof to daughter cells of the host cell. Host cells containing the transformed nucleic acids or fragments thereof are referred to herein as "transgenic" or "recombinant" or "transformed" cells.

The term "promoter" refers to a polynucleotide sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a nucleic acid in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid molecule so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The terms "plasmid" and "vector" refer to a nucleic acid element usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Suitable vectors can be chosen or constructed, containing appropriate regulatory sequences, including promoter sequences, terminator sequences, polyadenylation sequences, enhancer sequences, marker genes and other sequences as appropriate.

The term "expression", as used herein, refers to the transcription and stable accumulation of sense (mRNA) or antisense RNA derived from the nucleic acid molecules of the invention. Expression may also refer to translation of mRNA into a polypeptide.

As used herein, the term a "heterologous protein" refers to a protein (e.g. a polypeptide, peptide or fragment thereof) that is encoded by a heterologous nucleic acid and expressed in a host cell. A heterologous protein may be expressed transiently (e.g. where the polynucleotide encoding the heterologous protein does not incorporate into the host cell genome) or stably (e.g. where the polynucleotide encoding the heterologous protein incorporates into the host cell genome).

As used herein, the term "antibody" (or a fragment, variant, or derivative thereof) refers to at least the minimal portion of an antibody which is capable of binding to antigen, e.g., at least the variable domain of a heavy chain (VH) and the variable domain of a light chain (VL) in the context of a typical antibody produced by a B cell. Basic antibody structures in vertebrate systems are relatively well understood. See, e.g., Harlow et al., Antibodies: A Laboratory Manual, (Cold Spring Harbor Laboratory Press, 2nd ed. 1988), which is incorporated by reference herein in its entirety.

Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019, which is incorporated by reference herein in its entirety. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibodies or antigen-binding fragments, variants, or derivatives thereof disclosed herein can be described or specified in terms of the epitope(s) or portion(s) of an antigen, e.g., a target polypeptide that they recognize or specifically bind. For example, an IL-13 or anti-IL -13 antibody is an antibody that binds to an IL-13 polypeptide or a portion thereof. In some aspects, the anti-IL-13 antibody is BAK502G9 (e.g. an anti-IL-13 antibody comprising SEQ ID NOs: 1 and 2). In one embodiment, the antibody is BAK502G9 (as represented by the VH and VL domains of SEQ ID NOs 1-2 and/or the heavy and light chain CDRs of SEQ ID NOs 3-8), BAK278D6 (as represented by the VH and VL domains of SEQ ID NOs 9-10 and/or the heavy and light chain CDRs of SEQ ID NOs 11-16), BAK1183H4 (as represented by the VH and VL domains of SEQ ID NOs 17-18 and/or the heavy and light chain CDRs of SEQ ID NOs 19-24), or BAK1167F2 (as represented by the VH and VL domains of SEQ ID NOs 25-26 and/or the heavy and light chain CDRs of SEQ ID NOs 27-32).

Other anti-IL-13 monoclonal antibodies that can be used include those described in U.S. Pat. Appl. Publ. No. 2012-0052060, published Mar. 1, 2012, herein incorporated by reference in its entirety. Other IL-13 antibodies include, without limitation, anti-human-IL-13 antibodies, for example, Lebrikizumab (MILR1444A/RG3637, Roche/Genentech), ABT-308 (Abbott), GSK679586 (GlaxoSmithKline) or QAX576 (Novartis). As is well known in the art, antibodies, including anti-IL13 antibodies, may be produced in cells using various techniques known in the art. See, e.g., Monoclonal Antibodies, Hybridomas: A New Dimension in Biological Analyses, Kennet et al.(eds.) Plenum Press, New York (1980); and Antibodies: A Laboratory Manual, Harlow and Lane (eds.), Cold Spring Harbor Laboratory Press, Cold Spring Harbor, N.Y. (1988).

DESCRIPTION OF THE EMBODIMENTS

I. Cell Culture Medium

Cell culture is the process of placing cells, tissues, or organs removed from an animal into an artificial environment that promotes their survival, growth, and/or proliferation. Basic environmental requirements for cells to grow optimally include: a suitable vessel, a cell culture / growth medium to supply nutrients (including, but not limited to, at least one of amino acids, carbohydrates, vitamins, minerals, growth factors, hormones, etc.), and a controlled physicochemical environment (to control, e.g., pH, osmotic pressure, temperature, $O_2$, $CO_2$, etc.). Some cells are anchorage-dependent and must be cultured while attached to a solid or semi-solid substrate (adherent or monolayer culture), while others can be grown floating in the culture medium (suspension culture). One step in cell culture is selecting an appropriate growth medium. The cell culture medium or cell culture method according to the embodiments disclosed herein includes a cell culture medium sufficient to support cell growth comprising N-acetylcysteine. In one embodiment, the cell culture medium is a serum free and animal-protein free medium. In one embodiment, the cell culture medium is a chemically-defined medium. In another embodiment, N-acetylcysteine is added to commercially-available cell culture media. In one embodiment, the commercially-available cell culture medium is EX-CELL® NS0 serum-free medium for NS0 cells (available from Sigma-Aldrich, catalog number H4281), EX-CELL® CD hybridoma medium (Sigma-Aldrich, catalog number H4409), Ex-Cell 620-HSF serum-free medium for hybridoma cells (Sigma-Aldrich, catalog number 14621C), Ex-Cell NS- serum-free medium for NS0 (Sigma-Aldrich, catalog number 14650C), DMEM (Sigma-Aldrich, catalog number D567), Iscove's Modified Dulbecco's Medium (IMDM) (available from Sigma-Aldrich, catalog number 13390), RPMI-1640 Medium (Sigma-Aldrich, catalog number R8005), Hybridoma-SFM (Life Technologies, catalog number 12045076), CD Hybridoma AGT medium (Life Technologies, catalog number 12372025), CD Hybridoma medium (available from Life Technologies, catalog number 11278023), PFHM-II protein-free hybridoma medium (Life Technologies, catalog number 12040077), Nutridoma-SP (Roche, catalog number 11011374001), UltraDOMA-PF hybridoma medium (Lonza, catalog number 12-727F), UltradDOMA serum free hybridoma media (Lonza, catalog number 12-723B), Hyclone PF-Mab media (GE Life Sciences, SH30138.05), Hyclone SFM4MAb media (GE Life Sciences SH30391.02), Hyclone SFM4Mab-utility media (GE Life Sciences, catalog no SH30382.02), Hyclone ADCF-Mab media (GE Life Sciences, catalog number SH30349.02), Hyclone CCM1 media (GE Life Sciences, SH30043.03), HyClone CCM4MAb media (GE Life Sciences, SH30800.06), Hyclone CDM4NS0 media (GE Life Sciences, SH30478.06), and the like. In another embodiment, N-acetylcysteine is added to cell culture medium prepared from component ingredients with sterile deionized water as the basis for the medium.

A. N-acetylcysteine

N-acetylcysteine is added to the cell culture medium or the cell culture methods described herein to increase cell viability, cell growth rate, and/or reduce cell doubling time. While not being limited by any particular theory, it is believed that N-acetylcysteine provides benefits to cells growing in culture by protecting them from free radicals, preventing cell membrane breakdown, and/or preventing oxidation of other cell culture medium ingredients, including, but not limited to, lipids (such as cholesterol).

In one embodiment, a cell culture medium or a cell culture method as described herein comprises N-acetylcysteine at a concentration of from about 0.25 mM to about 3 mM, from about 0.5 mM to about 2.5 mM, from about 0.5 mM to about 2.0 mM, from about 0.5 mM to about 1.5 mM, from about 0.5 mM to about 1.0 mM, from about 1.0 mM to about 2.5 mM, from about 1.0 mM to about 2.0 mM, from about 1.0 mM to about 1.5 mM, from about 1.5 mM to about 2.5 mM, or from about 1.5 mM to about 2.0 mM. In one embodiment, a cell culture medium or a cell culture method as described herein comprises N-acetylcysteine at a concentration of about 1 mM. In another embodiment, a cell culture medium or a cell culture method as described herein comprises N-acetylcysteine at a concentration of about 1.5 mM. In another embodiment, a cell culture medium or a cell culture method as described herein comprises N-acetylcysteine at a concentration of about 2.0 mM. In another embodiment, a cell culture medium or a cell culture method as described herein comprises N-acetylcysteine at a concentration of about 2.5 mM. In another embodiment, a cell culture medium or a cell culture method as described herein comprises N-acetylcysteine at a concentration of about 0.5 mM. In another embodiment, the cell culture medium or a cell culture method as described herein comprises N-acetylcysteine at a concentration of at least about 0.5 mM, at least about 1.0 mM, at least about 1.5 mM, at least about 2.0 mM, or at least about 2.5 mM.

B. Other Cell Culture Medium Components

In some embodiments, the cell culture medium or cell culture method described herein further comprises a carbon source, a nitrogen source, and/or a phosphorous source. These can be provided by the same ingredient or different ingredients. In one embodiment, the cell culture medium or cell culture methods described herein further comprise a carbon source, a nitrogen source, a phosphorous source, and/or mineral salts. A carbon source suitable for use in the cell culture medium or cell culture methods described herein includes a carbohydrate (such as a sugar) or an amino acid, such as L-glutamine and/or pyruvate or any combination thereof. In one embodiment, the cell culture medium or cell culture method described herein further comprises carbohydrates and amino acids. In one embodiment, the cell culture medium or cell culture method described herein further comprises at least one of salts, vitamins, metabolic precursors, growth factors, hormones, and trace elements. In some embodiments, the cell culture medium or cell culture methods described herein further comprise basal media, containing amino acids, vitamins, inorganic salts, and a carbon source such as glucose.

1. Carbohydrates

Exemplary carbohydrates suitable for use in the cell culture medium or cell culture methods described herein include glucose, galactose, trehalose, glucosamine, mannose, raffinose, fructose, ribose, glucuronic acid, lactose, maltose, sucrose, turanose, any other carbohydrate suitable for cell culture generally known in the art, or any combinations thereof. In one aspect, the carbohydrate may be glucose or galactose.

2. Amino Acids

Exemplary amino acids suitable for use in the cell culture medium or cell culture methods described herein include one or more essential amino acids (i.e. histidine, isoleucine, leucine, lysine, methionine, phenylalanine, threonine, tryptophan, and/or valine), and/or one or more nonessential amino acids (i.e. alanine, arginine, aspartic acid, cysteine, glutamic acid, glutamine, glycine, proline, serine, tyrosine, and asparagine), and/or any combination of essential and non-essential amino acids thereof. For certain cells, some nonessential amino acids are essential amino acids because the cell does not have the capability of synthesizing that amino acid. For example, NS0 cells lack or contain very low levels of the endogenous glutamine synthetase enzyme and, as such, glutamine is an essential amino acid for NS0 cells unless glutamine synthetase is included in the expression system for a heterologous protein.

By amino acids, this disclosure includes any amino acids, including, but not limited to, D- or L-amino acids and non-standard amino acids. Thus, the term amino acid encompasses any organic compound with an amine (—$NH_2$) and a carboxylic acid (—COOH) functional group.

3. Lipids

In one embodiment, the cell culture medium or cell culture methods described herein further comprise a lipid. Exemplary lipids suitable for use in the cell culture medium or cell culture methods described herein include one or more of cholesterol, arachadonic acid, tocopherol acetate, linoleic acid, linolenic acid, myristic acid, oleic acid, palmitic acid, palmitoleic acid, stearic acid, a phospholipid (such as phosphatidylcholine) any other lipid suitable for cell culture generally known in the art, or any combinations thereof. Inositol, as a component of membrane phospholipids, may also be optionally included. Synthetic or plant-derived lipids may also be optionally used in applications where the medium is desired to be kept free of animal-derived components. Lipids may be added in a cyclodextrin-based lipid supplement. Cyclodextrins may be used to solubilize lipids and/or other ingredients such as fat-soluble vitamins and hormones.

Cholesterol may be synthetically produced or it may be animal derived. For instance, cholesterol may be isolated from sheep wool. An animal-protein free medium may contain cholesterol derived from an animal source. In some embodiments, cholesterol is obtained from a commercial source. See, e.g., Chemically Defined Lipid Concentrate from Gibco; Lipid Concentrate from SAFC. Cholesterol may be added to the medium in a cholesterol-cyclodextrin solution, as a synthetic cholesterol (such as but not limited to SyntheChol™), as cholesterol nanoparticles (see, e.g., Wu et al., Enhanced Productivity of NS0 cells in fed-batch culture with cholesterol nanoparticle supplementation, Biotechnology Progress 27(3):796-802 (2011)) or by any means suitable for cell culture generally known in the art.

In one embodiment, the medium may contain from about 1 to about 10 g/L of cholesterol. In another embodiment, the medium may contain from about 1 to about 5 g/l of cholesterol. In another embodiment, the medium may contain from about 1.5 to about 4 g/l of cholesterol. In another embodiment, the medium may contain from about 2 to about 3 g/l of cholesterol. In another embodiment, the medium may contain about 2.5 g/l of cholesterol. In another embodiment, the medium may contain at least about 1 g/L of cholesterol, at least about 2.5 g/L of cholesterol or at least about 5 g/L of cholesterol.

In another embodiment, the medium may contain a lipid other than cholesterol. In one embodiment, the medium may contain a phospholipid. In another embodiment, the medium may contain phosphatidylcholine. In one embodiment, the medium may contain from about 1 to about 10 g/L of phosphatidylcholine. In another embodiment, the medium may contain from about 1 to about 5 g/l of phosphatidylcholine. In another embodiment, the medium may contain from about 1.5 to about 4 g/l of phosphatidylcholine. In another embodiment, the medium may contain from about 2 to about 3 g/l of phosphatidylcholine. In another embodiment, the medium may contain about 2.5 g/l of phosphatidylcholine.

4. Salts

In one embodiment, the cell culture medium or cell culture methods described herein further comprise a salt. Exemplary salts suitable for use in the cell culture medium or cell culture methods described herein include at least one of calcium chloride, magnesium chloride, potassium chloride, sodium chloride, potassium nitrate, any other salt suitable for cell culture generally known in the art, or any combinations thereof.

In another embodiment, the cell culture medium or cell culture methods described herein do not include calcium chloride or magnesium chloride. This embodiment has advantages when cell dissociation or release is desired as calcium and magnesium promote cell adhesion.

5. Vitamins

In one embodiment, the cell culture medium or cell culture methods described herein further comprise a vitamin. Exemplary vitamins suitable for use in the cell culture medium or cell culture methods described herein include fat-soluble vitamins, vitamins A, D, E, K, B1 (thiamine), B2 (riboflavin), B3 (nicotinamide), B5 (pantothenic acid), B6 (pyridoxal, pyridoxamine, and/or pyridoxine), B9 (folic acid), any other vitamin suitable for cell culture generally known in the art, or any combinations thereof.

6. Growth Factors and Hormones

In one embodiment, at least one hormone may be added to the cell culture medium or cell culture methods described herein. In one embodiment, the hormone may be chosen from at least one of dexamethasone, erythropoietin, estradiol, hydrocortisone, insulin, progesterone, somatostatin, thyroxine (T4), triiodothyronine (T3), activin, BMP4, BMP7, BMPR1A, Cripto, FLT3 ligand, HGF, IGF, EGF, FGF, PDGF, IGFBP4, kallekrein, LEFTY-A, NGF, TGFβ, VEGF, or any other hormone or growth factor suitable for cell culture generally known in the art.

7. Trace Elements

In one embodiment, at least one trace element may be added to the cell culture medium or cell culture methods described herein. In one embodiment, the trace element may be at least one of zinc, iron, copper, selenium, magnesium, manganese, molybdenum, tin, nickel, or any other trace element suitable for cell culture generally known in the art.

8. Surfactants

In another embodiment, the cell culture medium or cell culture methods described herein further comprise at least one surfactant. Exemplary surfactants suitable for use in the cell culture medium or cell culture methods described herein include Tween-80, pluronic F-68, or any other surfactant suitable for cell culture generally known in the art.

9. Buffers

In another embodiment, the cell culture medium or cell culture methods described herein further comprise at least one pH buffering agent. Exemplary buffering agents suitable for use in the cell culture medium or cell culture methods described herein include sodium bicarbonate, boric acid, citric acid, dithiothreitol, ethanolamine, glycerophosphate, potassium citrate, potassium phosphate, sodium acetate, sodium chloride, sodium phosphate, starch from wheat, HEPES, calcium chloride, MOPS, or any other buffering agent cell suitable for cell culture generally known in the art, or any combination thereof.

10. Other Ingredients

In one embodiment, the cell culture medium or cell culture methods described herein further comprise a non-animal-sourced hydrolysate. For example a plant or yeast hydrolysate provides protein digests comprising amino acids, short peptides, carbohydrates, vitamins, nucleosides, and minerals, providing a variety of nutritional supplements to media. For example, yeastolate, a yeast hydrolysate, may be employed. Yeastolate is a mixture of peptides, amino acids, carbohydrates, lipids, metals and vitamins. It may be added in addition to or in lieu of those ingredients provided separately. In one embodiment, the cell culture medium comprises 1 g/L of yeastolate.

In one embodiment, tropolone may also be added to the cell culture medium or cell culture methods described herein. In another mode, nucleosides may be added to the cell culture medium or cell culture methods described herein. In another embodiment, β-mercaptoethanol may be added to the cell culture medium or cell culture methods described herein. In another embodiment, antibiotics may be added to the cell culture media or cell culture methods described herein.

In some embodiments, the cell culture medium or cell culture methods described herein contain NAC, an amino acid, a vitamin, a lipid, a carbohydrate, a pH buffering agent, a trace metal, an inorganic salt, and a surfactant. In one embodiment, the lipid is cholesterol.

II. Cell Culture Methods

A. Cell Types

A variety of cell types, such as cholesterol auxotrophic cells, myeloma cells, and hybridoma cells, may be cultured with the presently-disclosed cell culture medium comprising N-acetylcysteine. In one embodiment, the cells being cultured are derived from a mammal, including, but not limited to, cells derived from a mouse, rat, human, monkey, hamster, rabbit, etc.

As used herein, the term "cholesterol auxotroph" refers to a cell or cell line that requires cholesterol for growth but is unable to synthesize it. In one embodiment, a cholesterol auxotroph is NS0, NS1, U937, M19, SRD-12B, SRD-13A, CHO-215, X63 cells, cell lines derived from these cells lines, or any other cell engineered to be a cholesterol auxotroph. In another embodiment, the cells are NS0 cells.

In one embodiment, the cells suitable to be cultured with the presently-disclosed cell culture medium comprising N-acetylcysteine are cells that are cholesterol auxotrophs. In one embodiment, the cells suitable to be cultured with the presently-disclosed cell culture medium comprising N-acetylcysteine are NS0 cells. In another embodiment, the cells are NS1, U937, M19, SRD-12B, SRD-13A, CHO-215, X63 cells, cells derived from these cell lines, or any other cell engineered to be a cholesterol auxotroph. In another embodiment, the cells suitable to be cultured with the presently-disclosed cell culture medium comprising N-acetylcysteine are murine myeloma cells that are cholesterol auxotrophs. In one embodiment, the cells are mammalian myeloma cells that are cholesterol auxotrophs. In one embodiment the cells suitable to be cultured with the presently-disclosed cell culture medium comprising N-acetylcysteine are human myeloma cells that are cholesterol auxotrophs.

In one embodiment, the cells suitable to be cultured with the presently-disclosed cell culture medium comprising N-acetylcysteine are myeloma cells. In another embodiment, the cells are X63Ag8, Sp2/0, NS1, NS0, J558L, U266, U937, P3U1, XG-1, XG-2, XG-3, XG-4, XG-5, XG-6, XG-7, XG-8, XG-9, U266, RPM1-8226, LP1, L363, OPM1, OPM2, and NCLH929 cells or cell lines derived from these cells lines. In another embodiment, the cells suitable to be cultured with the presently-disclosed cell culture medium comprising N-acetylcysteine are hybridoma cells. In some aspects, the hybridoma cells suitable to be cultured with the presently-disclosed cell culture medium comprising N-acetylcysteine express and/or secrete an antibody.

B. Biologic Therapeutics

In one embodiment, the cells suitable to be cultured with the presently-disclosed cell culture medium comprising N-acetylcysteine (e.g. cholesterol auxotrophs, myeloma cells, or hybridomas, including NS0 cells) are cultured without inducing and/or expressing a recombinant or heterologous protein. In one embodiment, the cells suitable to be cultured with the presently-disclosed cell culture medium comprising N-acetylcysteine (e.g. cholesterol auxotrophs, myeloma cells, or hybridomas, including NS0 cells) are transformed with a heterologous nucleic acid (including, but not limited to cDNA, a plasmid, a vector, nucleic acids operably linked to a promoter, and/or nucleic acids that transiently express a heterologous nucleic acid or incorporate the heterologous nucleic acid into the genome of the cell line). In another method, the cells express a recombinant or heterologous protein. In one method, the cells overexpress the recombinant or heterologous protein. Cell lines expressing a wide variety of heterologous sequences may benefit from the present cell culture medium and method.

In one embodiment, the heterologous protein is transiently expressed. In another embodiment, the heterologous protein is stably expressed.

In one embodiment, the heterologous protein is not an antibody or antigen-binding fragment thereof. In one embodiment, the heterologous protein is a blood factor, anticoagulant, thrombolytic, erythropoietin, interferon, hormone, enzyme, vaccine, growth factor, and/or a fusion protein.

In another embodiment, the cells suitable to be cultured with the presently-disclosed cell culture medium comprising N-acetylcysteine (e.g. cholesterol auxotrophs, myeloma cells, or hybridomas, including NS0 cells) express a heterologous protein, wherein the heterologous protein is an antibody or antigen-binding fragment thereof. In one embodiment, the antibody or antigen-binding fragment thereof specifically binds IL-13 or specifically binds IL-9. In another embodiment, the antibody or antigen-binding fragment is an antibody or antigen-binding fragment disclosed in U.S. Pat. Nos. 7,947,273, 7,354,584 or 7,371,383, each herein incorporated by reference in their entirety. In another embodiment, the antibody is BAK502G9 (comprising SEQ ID NOs 1 and 2). In another embodiment, the antibody or antigen-binding fragment thereof has the same CDRs as BAK502G9 (comprising heavy chain CDRS (SEQ ID NOs: 3-5) and light chain CDRs (SEQ ID NOs: 6-8)). In another embodiment, the antibody or antigen binding fragment has a heavy chain variable region comprising any one of SEQ ID NOs: 1, 9, 17, or 25 and a light chain variable region comprising any one of SEQ ID NOs: 2, 10, 18, or 26. In another embodiment, the antibody or antigen binding fragment has a heavy chain variable region comprising: (a) a HC CDR1 chosen from SEQ ID NOs: 3, 11, 19, and 27; (b) a HC CDR2 chosen from SEQ ID NOs: 4, 12, 20, and 28; and (c) a HC CDR chosen from SEQ ID NOs: 5, 13, 21, and 29; and a light chain variable region comprising: (a) a LC CDR1 chosen from SEQ ID NOs: 6, 14, 22, and 30; (b) a LC CDR2 chosen from SEQ ID NOs: 7, 15, 23, and 31; and (c) a LC CDR3 chosen from SEQ ID NOs: 8, 16, 24, and 32. In another embodiment, the antibody or antigen binding fragment comprises a heavy chain variable region (VH) and/or a light chain variable region (VL) described in Table 1; or comprises a set of 6 of the CDRs described in Table 1.

In another embodiment, the antibody or antigen binding fragment has a heavy chain variable region comprising a sequence that is about 70%, about 75%, about 80%, about 85%, about 90%, about 92%, about 93%, about 94%, about 98%, or about 99% identical to any one of SEQ ID NOs: 1, 9, 17, or 25 and a light chain variable region comprising a sequence that is about 70%, about 75%, about 80%, about 85%, about 90%, about 92%, about 93%, about 94%, about 98%, or about 99% identical to any one of SEQ ID NOs: 2, 10, 18, or 26. In another embodiment, the antibody or antigen binding fragment has a heavy chain variable region comprising: (a) a HC CDR1 that has one mutation compared to a sequence chosen from SEQ ID NOs: 3, 11, 19, or 27; (b) a HC CDR2 that has one or two mutations compared to a sequence chosen from SEQ ID NOs: 4, 12, 20, and 28; and (c) a HC CDR3 that has one or two mutations compared to a sequence chosen from SEQ ID NOs: 5, 13, 21, and 29; and a light chain variable region comprising: (a) a LC CDR1 that has one mutation compared to a sequence chosen from SEQ ID NOs: 6, 14, 22, and 30; (b) a LC CDR2 that has one or two mutations compared to a sequence chosen from SEQ ID NOs: 7, 15, 23, and 31; and (c) a LC CDR3 that has one or two mutations compared to a sequence chosen from SEQ ID NOs: 8, 16, 24, and 32. In another embodiment, the antibody or antigen binding fragment has a heavy chain variable region (VH) and/or a light chain variable region (VL) comprising a sequence that is about 70%, about 75%, about 80%, about 85%, about 90%, about 92%, about 93%, about 94%, about 98%, or about 99% identical to any one of the VH and/or VL sequences described in Table 1. In some embodiments, the antibody or antigen binding fragment has one or two mutations in a CDR compared to any one of the CDRs described in Table 1.

In another embodiment, the antibody or antigen binding fragment thereof specifically binds glycoprotein IIb/IIIa, IL-2 receptor (such as the IL-2 receptor a), TNF-α, RSV, F protein epitope of RSV, CD33, epidermal GF receptor, T-cell VLA4 receptor, complement protein C5, IL-1, IL-9, IL-12, IL-13, IL-23, CD-20, and/or BAFF.

In a further embodiment, the antibody or antigen binding fragment thereof is ofatumumab, belimumab, gemtuzumab ozogamicin, palivizumab, natalizumab, cetuximab, canakinumab, infliximab, abciximab, basiliximab, daclizumab, eculizumab, or ustekinumab.

C. Cell Culture Processes

In one embodiment, a cell culture method comprises providing a cell culture medium sufficient to support cell growth, wherein the cell culture medium comprises N-acetylcysteine and culturing a cell in the cell culture medium, wherein the cell is a cholesterol auxotroph, a myeloma, or a hybridoma. In one embodiment, the method is a method of increasing cell viability, increasing cell growth rate, and/or reducing cell doubling time of a cell by providing a cell culture medium sufficient to support cell growth comprising N-acetylcysteine; and culturing the cell in the cell culture medium, wherein the cell is a cholesterol auxotroph, a myeloma, or a hybridoma.

In one embodiment, the cells are cultured at 37° C. at 5% $CO_2$ and 85% relative humidity. In one embodiment the pH may be from 6.8 to 7.4. Other acceptable conditions generally known in the art may also be used.

In one aspect, the cell culture occurs while scaling up production from a frozen stock to a large bioreactor. In one aspect, the improved medium allows for at least a four-fold split ratio when passaging the cells (namely 1× of cell culture medium containing the cells to be passaged is mixed with 3× of fresh cell culture medium not containing the cells). In another aspect, it allows for a five-fold split ratio, six-fold split ratio, or a seven-fold split ratio.

In one embodiment, the cells are cultured in a 100 L bioreactor, then transferred to a 500 L bioreactor, and then transferred to a 2500 L bioreactor.

In one embodiment, the cells (e.g. cholesterol auxotrophs, myelomas, or hybridomas) are thawed from a frozen stock. In one embodiment, the cells (e.g. cholesterol auxotrophs, myelomas, or hybridomas) are in an expansion phase. In another embodiment, the cells (e.g. cholesterol auxotrophs, myelomas, or hybridomas) are grown in a batch mode, a fed-batch mode, continuous culture, perfusion, or in an integrated bioreactor-purification unit.

D. Impact on Cell Culture Efficiency

The present cell culture method and/or media may provide multiple advantages. In one instance, it reduces the time required for cells (e.g. cholesterol auxotrophs, myelomas, or hybridomas such as NS0 cells) to grow in a vessel (such as a bioreactor) by at least about 10% to at least about 50% (e.g. at least about 10%, about 15%, about 20%, about 25%, about 30%, about 35%, about 40%, about 45%, or about 50%) compared to a cell culture medium without N-acetylcysteine. In one embodiment, this is determined by calculating the period of time necessary to get to a desired cell count per volume.

In another embodiment, the cell culture method and/or media reduce the average cell doubling time of a cholesterol auxotroph, a myeloma, or a hybridoma (e.g. NS0 cells) cultured using a cell culture method and/or media comprising N-acetylcysteine compared to a cholesterol auxotroph, a myeloma, or a hybridoma (e.g. NS0 cells) cultured in a cell culture with a control medium excluding N-acetylcysteine. In one embodiment, the average doubling time of a cholesterol auxotroph, a myeloma, or a hybridoma (e.g. NS0 cells) cultured using a cell culture method and/or media comprising N-acetylcysteine is shorter than a cholesterol auxotroph, a myeloma, or a hybridoma (e.g. NS0 cells) cultured in a cell culture with a control medium excluding N-acetylcysteine. In another embodiment, the average and/or median cell doubling time of a cholesterol auxotroph, a myeloma, or a hybridoma (e.g. NS0 cells) cultured using a cell culture method and/or media comprising N-acetylcysteine is reduced by at least about 10% to at least about 50% (e.g. at least about 10%, about 15%, about 20%, about 25%, about 30%, about 35%, about 40%, about 45%, or about 50%) compared to a cholesterol auxotroph, a myeloma, or a hybridoma (e.g. NS0 cells) cultured in a cell culture medium without N-acetylcysteine. In one aspect, the average and/or median cell doubling time of a cholesterol auxotroph, a myeloma, or a hybridoma (e.g. NS0 cells) cultured using a cell culture method and/or media comprising N-acetylcysteine is less than or equal to 60 hours to less than or equal to about 29 hours (e.g. less than or equal to about 60 hours, about 42 hours, about 34 hours, about 30 hours, or about 29 hours) or about less than or about equal to any of the average cell doubling times reported in FIGS. 1-12.

In one embodiment, the cell doubling time may be determined by counting the cells in a given cell culture medium at multiple time intervals and plotting the data on a graph. Average doubling time can be calculated by averaging the doubling time values in the exponential growth phase in multiple replicate cultures using the equation $DT = T \ln 2 / \ln(X2/X1)$, where DT=doubling time, T is the incubation time in any units; X1 is the cell number at the beginning of the incubation time, and X2 is the cell number at the end of the incubation time.

In an additional embodiment, the cell culture method and/or media increase the cell growth rate of a cholesterol auxotroph, a myeloma, or a hybridoma (e.g. NS0 cells) cultured using a cell culture method and/or media comprising N-acetylcysteine compared to a cholesterol auxotroph, a myeloma, or a hybridoma (e.g. NS0 cells) cultured in a cell culture with a control medium excluding N-acetylcysteine. In one embodiment, the cell growth rate of a cholesterol auxotroph, a myeloma, or a hybridoma (e.g. NS0 cells) cultured using a cell culture method and/or media comprising N-acetylcysteine is higher than a cholesterol auxotroph, a myeloma, or a hybridoma (e.g. NS0 cells) cultured in a cell culture with a control medium excluding N-acetylcysteine. In another embodiment, cell growth rate of a cholesterol auxotroph, a myeloma, or a hybridoma (e.g. NS0 cells) cultured using a cell culture method and/or media comprising N-acetylcysteine is increased by at least about 10% to at least about 50% (e.g. at least about 10%, about 15%, about 20%, about 25%, about 30%, about 35%, about 40%, about 45%, or about 50%) compared to a cholesterol auxotroph, a myeloma, or a hybridoma (e.g. NS0 cells) cultured in a cell culture medium without N-acetylcysteine.

In one embodiment, cell growth may be determined using a cell counting method. In one embodiment, a sample volume of cell culture medium is obtained and the cells counted in that volume. Cell counting may be done in a hemocytometer or with a Coulter Counter. Another method plots the number of cells against time, with the slope of the graph stepper for cultures showing improved growth rates.

In another embodiment, the cell culture method and/or media disclosed herein increase the cell viability of a cholesterol auxotroph, a myeloma, or a hybridoma (e.g. NS0 cells) over a cholesterol auxotroph, a myeloma, or a hybridoma (e.g. NS0 cells) cultured in a cell culture with a control medium excluding N-acetylcysteine. In one embodiment, cell viability of a cholesterol auxotroph, a myeloma, or a hybridoma (e.g. NS0 cells) cultured using a cell culture method and/or media comprising N-acetylcysteine is higher compared to a cholesterol auxotroph, a myeloma, or a hybridoma (e.g. NS0 cells) cultured in a cell culture with a control medium excluding N-acetylcysteine. In one embodiment, cell viability of a cholesterol auxotroph, a myeloma, or a hybridoma (e.g. NS0 cells) cultured using a cell culture method and/or media comprising N-acetylcysteine is increased by at least about 5% to at least about 15% (e.g. at least about 5%, about 7%, about 10%, about 12%, or about 15%) compared to a cholesterol auxotroph, a myeloma, or a hybridoma (e.g. NS0 cells) cultured in a cell culture medium without N-acetylcysteine. In one aspect, the cell viability of a cholesterol auxotroph, a myeloma, or a hybridoma (e.g. NS0 cells) cultured using a cell culture method and/or media comprising N-acetylcysteine is at least about 85% to at least about 95% (e.g. at least about 85%, about 88%, about 90%, about 92%, about 93%, about 94%, or about 95%).

In one embodiment, cell viability may be determined by a trypan blue viability exclusion assay. In such an assay, a cell suspension may be mixed with 0.4% trypan blue in phosphate buffered solution and cells counted using a hemocytometer. Live cells appear round and refractile without any blue-dye coloration, while dead cells absorb the dye and appear blue. Viability may be expressed as a percentage of viable cells over total cells counted, with a viable cell being a cell whose membrane integrity is still able to prevent the absorption of the trypan blue in a trypan blue exclusion viability assay.

In another embodiment, increased protein yield, such as increased heterologous protein expression, is obtained using the cell culture method and/or media disclosed herein. In one embodiment, recombinant or heterologous protein expression is higher in a cholesterol auxotroph, a myeloma, or a hybridoma (e.g. NS0 cells) cultured using a cell culture method and/or media comprising N-acetylcysteine compared to a cholesterol auxotroph, a myeloma, or a hybridoma (e.g. NS0 cells) cultured in a cell culture with a control medium excluding N-acetylcysteine. In one embodiment, the cholesterol auxotroph, myeloma, or hybridoma (e.g. NS0 cells) cultured using a cell culture method and/or media comprising N-acetylcysteine shows at least 10% to at least 200% (e.g. at least 10%, 20%, 30%, 40%, 50%, 60%, 70%, 80% 90%, 100%, 150%, 200%) higher protein expression compared to a cholesterol auxotroph, a myeloma, or a hybridoma (e.g. NS0 cells) cultured in a cell culture medium without N-acetylcysteine.

Reference will now be made in detail to the present exemplary embodiments, examples of which are illustrated in the accompanying drawings. Wherever possible, the same reference numbers will be used throughout the drawings to refer to the same or like parts. Other embodiments will be apparent to those skilled in the art from consideration of the specification and practice disclosed herein. The embodiments are further explained in the following examples. These examples do not limit the scope of the claims, but merely serve to clarify certain embodiments. It is intended that the specification and examples be considered as exemplary only, with a true scope and spirit being indicated by the following claims.

EXAMPLES

Example 1

Cell Doubling Time of NS0 Cell Line 1 in APF Medium 1 and 2 at Vial Thaw

To investigate the role of N-Acetylcysteine on thaw recovery, cell viability, cell growth and cell doubling time on subsequent passaging, the following methods were used. Three different NS0 cell lines cultured in one to three different Animal Protein Free ("APF") media were investigated to study the effect of N-acetylcysteine (NAC) on cell growth at vial thaw and during routine cell expansion. One of the cell lines was a NS0 null host cell that had not been transformed to express a recombinant protein (NS0 Null Cell Line). The other two NS0 cell lines were engineered to express a therapeutic recombinant protein: NS0 Cell Line 1 (expressing an anti-IL-9 antibody) and NS0 Cell Line 2 (expressing BAK502G9, an anti-IL-13 antibody). NS0 Cell Line 1 was thawed and expanded in two different APF media (APF Medium 1 or APF Medium 2) supplemented with various concentrations of NAC ranging from 1.5 mM to 2.5 mM. NS0 Cell Line 2 was thawed and expanded in three different APF media (APF Medium 1, APF Medium 2 or a commercially available NS0 cell culture media (CD Hybridoma+cholesterol from Invitrogen/Gibco)) supplemented with NAC ranging from 0.5 mM to 2.5 mM, while the untransformed host cell line (NS0 Null Cell Line) was thawed in APF medium 2 supplemented with NAC ranging from 0.5 mM to 1.5 mM. NAC was obtained from Sigma and was either added to the medium directly or dissolved in water at 100 mM concentration before adding to the media at the appropriate concentration. All three media (APF Medium 1, APF Medium 2, and CD Hybridoma+cholesterol from Invitrogen/Gibco) supported growth of NS0 cells, as illustrated in FIGS. 1-12. APF Medium 1 and APF Medium 2 contain standard cell culture components including: amino acids, vitamins, lipids, sugar, small peptides, pH buffer, trace metals, inorganic salts, nucleotides, nucleotide precursors, surfactants, reducing agents, cholesterol, lipids and antioxidants.

Prior to vial thaw, media were temperature and pH equilibrated for a minimum of 1 hour in a 6% CO2 incubator at 37° C. with agitation at 120 rpm on a shaker. Vials were thawed using a 37° C. water bath and the entire contents were transferred equilibrated media. A cell count using Beckman Vi-Cell (an image-based cell viability analyzer) was obtained to measure the viable cell density and viability.

Viable cell densities during the first 3 to 4 days (i.e. exponential growth phase) at each passage were used to calculate population doubling times during both the first few days after the vial thaw while the cells were recovering from the thaw and during subsequent cell passages when the cells have fully recovered and reached a consistent doubling time from passage to passage.

NS0 cells (i.e. NS0 Cell Line 1) expressing an anti-IL-9 monoclonal antibody were in a frozen stock. Frozen NS0 Cell Line 1 cells were thawed in animal-protein free (APF) medium (i.e. APF media 1 or APF media 2) supplemented with various concentrations of N-acetylcysteine (NAC) and viable cell density during exponential growth phase was used to calculate average cell doubling time as described above.

FIG. 1 shows NS0 Cell Line 1 cell doubling time in control medium (APF media 1 without NAC) and APF media 1 supplemented with three increasing concentrations of N-acetylcysteine for cells thawed from a frozen stock. Addition of 1.5 mM to 2.5 mM NAC (1.5 mM, 2.0 mM or 2.5 mM NAC) reduced average cell doubling time at vial thaw (55.6 hours, 48.4 hours, and 53.9 hours, respectively) compared to NS0 Cell Line 1 cells thawed in control medium (57.6 hours). While not being bound by theory, the slight increase in doubling time between 2 mM and 2.5 mM may be due to an increase in osmolality of the solution, especially as NS0 cells can be sensitive to osmolality during thawing.

Figure 2:
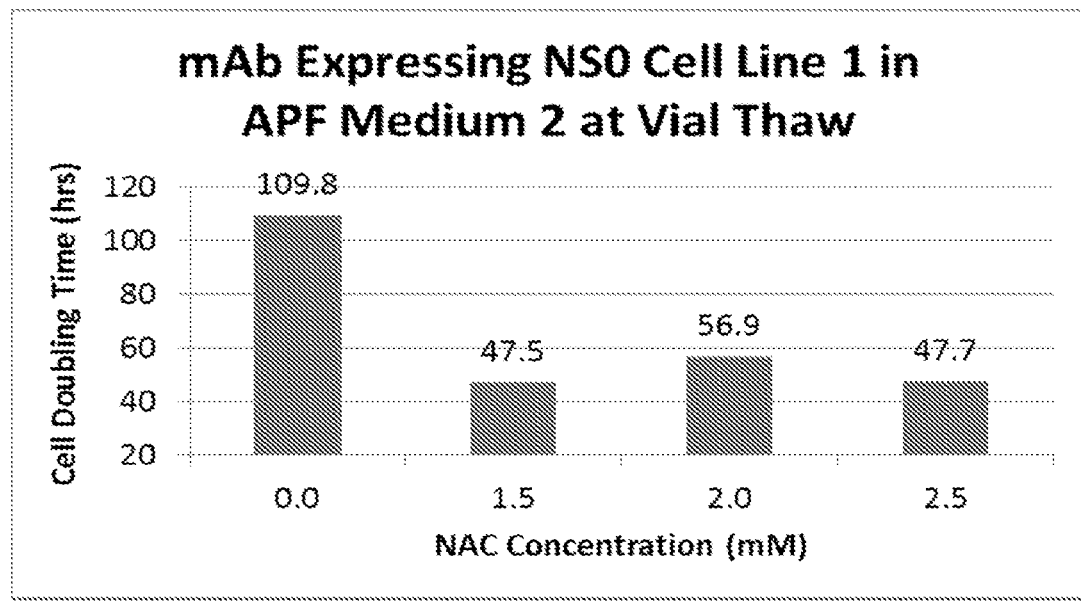
FIG. 2 shows population doubling time of NS0 Cell Line 1 expressing a monoclonal antibody ("mAb") against IL-9 in APF medium 2 at vial thaw. Frozen NS0 Cell Line 1 cells thawed in animal-protein free (APF) medium 2 were supplemented with N-acetylcysteine (NAC) (1.5 mM, 2.0 mM, or 2.5 mM) and viable cell density during exponential growth phase was used to calculate average doubling time. Addition of 1.5 mM to 2.5 mM NAC improved cell viability, increased cell growth and reduced average cell doubling time from vial thaw of NS0 Cell Line 1. hrs=hours; mM=millimolar.

FIG. 2 shows NS0 Cell Line 1 cell doubling time in control medium (APF media 2 without NAC) and APF media 2 supplemented with three increasing concentrations of N-acetylcysteine for cells thawed from a frozen stock. Similar to the results observed with APF Media 1, adding 1.5 mM to 2.5 mM NAC (1.5 mM, 2.0 mM or 2.5 mM NAC) to APF Media 2 also reduced cell doubling time at vial thaw (47.5 hours, 56.9 hours, and 47.7 hours, respectively) compared to NS0 Cell Line 1 cells thawed in control medium (109.8 hours).

These experiments show that addition of N-acetylcysteine (about 1.5 mM to about 2.5 mM; or about 1.5 mM, about 2.0 mM or about 2.5 mM) to the cell culture media of NS0 cells during vial thaw increases cell viability, cell growth and reduces cell doubling time.

Example 2

Cell Doubling Time of NS0 Cell Line 2 in APF Medium 1, APF Medium 2 and CD Hybridoma Media at Vial Thaw NS0 cells (i.e. NS0 Cell Line 2) expressing a monoclonal antibody (i.e. BAK502G9, an anti-IL-13 antibody) were in a frozen stock. Frozen NS0 Cell Line 2 cells were thawed in animal-protein free (APF) medium (i.e. APF media 1, APF media 2 or CD Hybridoma medium (Gibco) supplemented with cholesterol (1× Invitrogen Cholesterol Lipid Concentrate)) supplemented with various concentrations of N-acetylcysteine (NAC) and viable cell density during exponential growth phase was used to calculate average cell doubling time as described in Example 1.

Figure 3:
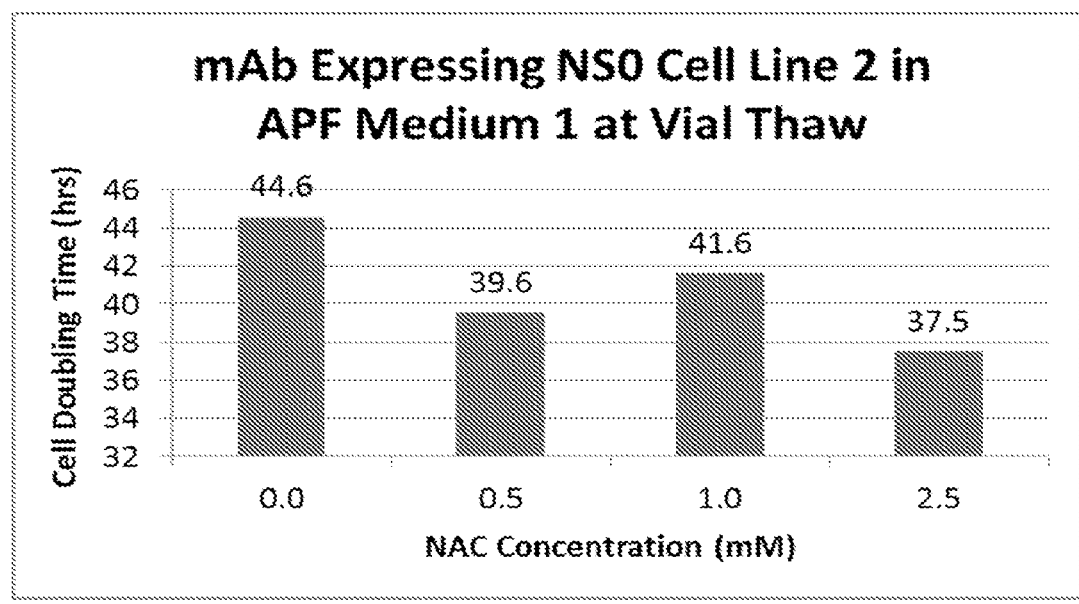
FIG. 3 shows population doubling time of NS0 Cell Line 2 expressing a monoclonal antibody ("mAb") against IL-13 in APF medium 1 at vial thaw. Frozen NS0 Cell Line 2 cells thawed in animal-protein free (APF) medium 1 were supplemented with N-acetylcysteine (NAC) (0.5 mM, 1.0 mM or 2.5 mM) and viable cell density during exponential growth phase was used to calculate average doubling time. Addition of 0.5 mM to 2.5 mM NAC improved cell viability, increased cell growth and reduced average cell doubling time from vial thaw of NS0 Cell Line 2. hrs=hours; mM=millimolar.

FIG. 3 shows NS0 Cell Line 2 cell doubling time in control medium (APF media 1 without NAC) and APF media 1 supplemented with three increasing concentrations of N-acetylcysteine for cells thawed from a frozen stock. Addition of 0.5 mM to 2.5 mM NAC (0.5 mM, 1.0 mM or 2.5 mM NAC) reduced average cell doubling time at vial thaw (39.6 hours, 41.6 hours, and 37.5 hours, respectively) compared to NS0 Cell Line 2 cells thawed in control medium (44.6 hours), with 2.5 mM NAC showing the greatest reduction of cell doubling time at vial thaw.

Figure 4:
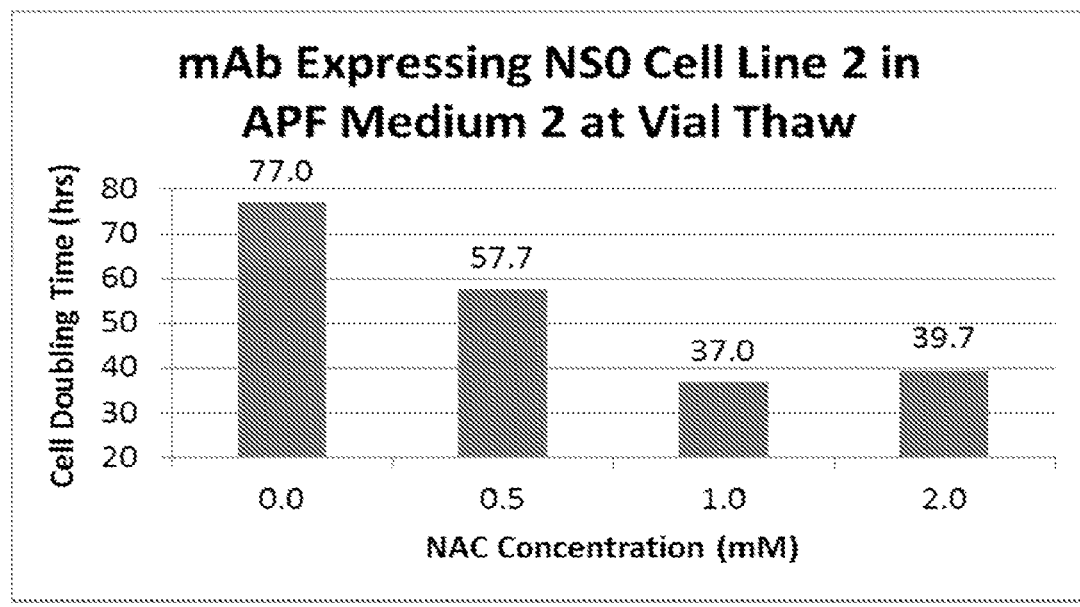
FIG. 4 shows population doubling time of NS0 Cell Line 2 expressing a monoclonal antibody ("mAb") against IL-13 in APF medium 2 at vial thaw. Frozen NS0 Cell Line 2 cells thawed in animal-protein free (APF) medium 2 were supplemented with N-acetylcysteine (NAC) (0.5 mM, 1.0 mM or 2.0 mM) and viable cell density during exponential growth phase was used to calculate average doubling time. Addition of 0.5 mM to 2.0 mM NAC improved cell viability, increased cell growth and reduced average cell doubling time from vial thaw of NS0 Cell Line 2. hrs=hours; mM=millimolar.

FIG. 4 shows NS0 Cell Line 2 cell doubling time in control medium (APF media 2 without NAC) and APF media 2 supplemented with three increasing concentrations of N-acetylcysteine for cells thawed from a frozen stock. Similar to the results observed with APF media 1, 0.5 mM to 2.0 mM NAC (0.5 mM, 1.0 mM or 2.0 mM NAC) reduced average cell doubling time at vial thaw (57.7 hours, 37.0 hours, and 39.7 hours, respectively) compared to NS0 Cell Line 2 cells thawed in control medium (77.0 hours), with 1.0 mM and 2.0 mM showing the greatest reduction of cell doubling time at vial thaw.

Figure 5:
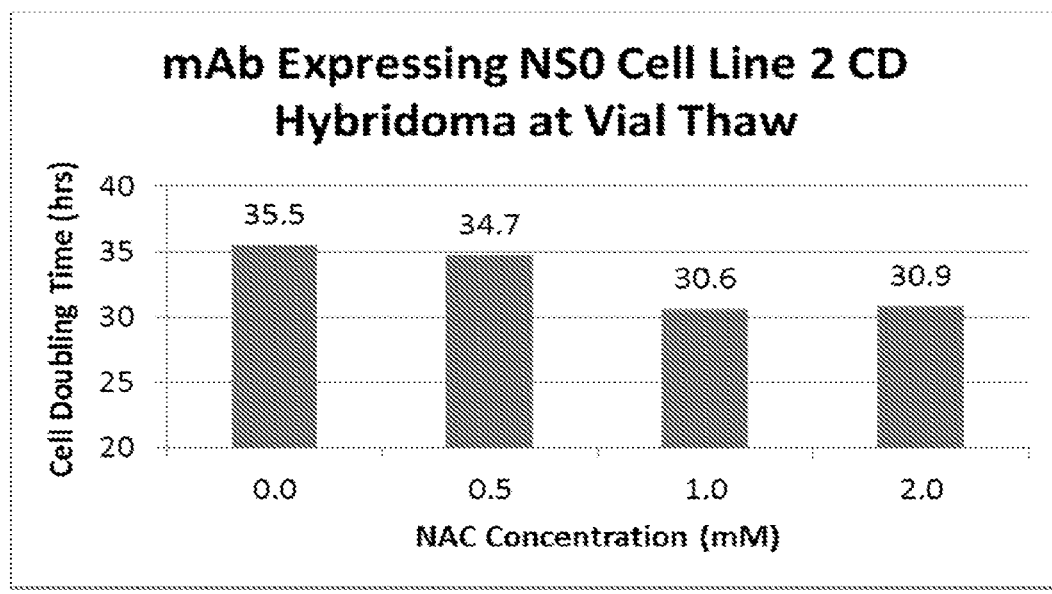
FIG. 5 shows population doubling time of NS0 Cell Line 2 expressing a monoclonal antibody against IL-13 in commercially available NS0 cell culture media (CD Hybridoma, Gibco) supplemented with cholesterol (1× Invitrogen Cholesterol Lipid Concentrate) at vial thaw. Frozen NS0 Cell Line 2 cells thawed in CD Hybridoma medium with 1× Cholesterol Lipid Concentrate were supplemented with N-acetylcysteine (NAC) (0.5 mM, 1.0 mM or 2.0 mM) and viable cell density during exponential growth phase was used to calculate average doubling time. Addition of 0.5 mM to 2.0 mM NAC improved cell viability, increased cell growth and reduced average cell doubling time of NS0 Cell Line 2. hrs=hours; mM=millimolar.

FIG. 5 shows NS0 Cell Line 2 cell doubling time in control medium (CD Hybridoma medium (Gibco) supplemented with 1× Invitrogen Cholesterol Lipid Concentrate without NAC) and control medium supplemented with three increasing concentrations of N-acetylcysteine for cells thawed from a frozen stock. Similar to the results observed with APF media 1 and APF media 2, addition of 1.0 mM to 2.0 mM NAC reduced average cell doubling time at vial thaw (34.7 hours, 30.6 hours, and 30.9 hours, respectively) compared to NS0 Cell Line 2 cells thawed in control medium (35.5 hours), with 1.0 mM and 2.0 mM showing the greatest reduction of cell doubling time at vial thaw.

These experiments show that addition of N-acetylcysteine (about 0.5 mM to about 2.5 mM; or about 0.5 mM, about 1.0 mM, about 2.0 mM or about 2.5 mM) to the cell culture media of NS0 cells at vial thaw increases cell viability, cell growth and reduces cell doubling time.

Example 3

Cell Doubling Time of NS0 Null Cell Line in APF Medium 2 at Vial Thaw

NS0 cells (i.e. NS0 Null Cell Line) not transfected with a heterologous protein were in a frozen stock. Frozen NS0 Null Cell Line cells were thawed in animal-protein free (APF) medium (i.e. APF media 2) supplemented with various concentrations of N-acetylcysteine (NAC) and viable cell density during exponential growth phase was used to calculate average cell doubling time as described in Example 1.

Figure 6:
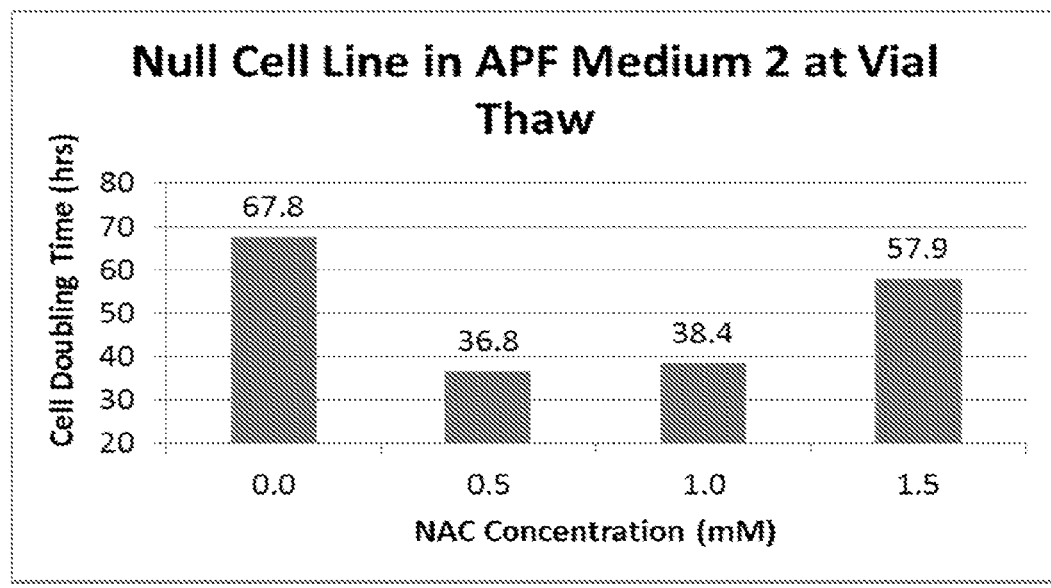
FIG. 6 shows population doubling time of an NS0 null cell line (an untransfected NS0 cell line not expressing a recombinant protein) in APF medium 2 at vial thaw. Frozen NS0 Null Cell Line cells thawed in animal-protein free (APF) medium 2 were supplemented with N-acetylcysteine (NAC) (0.5 mM, 1.0 mM or 1.5 mM) and viable cell density during exponential growth phase was used to calculate average doubling time. Addition of 0.5 mM to 1.5 mM NAC improved cell viability, increased cell growth and reduced average cell doubling time at vial thaw. hrs=hours; mM=millimolar.

FIG. 6 shows NS0 Null Cell Line cell doubling time in control medium (APF media 2 without NAC) and APF media supplemented with three increasing concentrations of N-acetylcysteine for cells thawed from a frozen stock. Similar to the results reported in Examples 1 and 2, addition of 0.5 mM to 1.5 mM NAC (0.5 mM, 1.0 mM or 1.5 mM NAC) reduced cell doubling time at vial thaw (36.8 hours, 38.4 hours and 57.9 hours, respectively) compared to NS0 Null Cell Line cells thawed in control medium (67.8 hours), with 0.5 mM and 1.0 mM showing the greatest reduction of cell doubling time at vial thaw.

These results, when taken together with the results summarized in Examples 1 and 2, reveal that three NS0 cell lines thawed in three different media supplemented with N-acetylcysteine at concentrations of 0.5 mM, 1.0 mM, 1.5 mM, 2.0 mM, and 2.5 mM (e.g. about 0.5 mM to about 2.5 mM) consistently showed increased cell viability, cell growth and reduced cell doubling time at vial thaw compared to NS0 cells thawed in control media.

Example 4

Cell Doubling Time of NS0 Cell Line 1 in APF Medium 1 and 2 During Cell Expansion NS0 cells (i.e. NS0 Cell Line 1) expressing an anti-IL-9 monoclonal antibody were cultured in animal-protein free (APF) medium (i.e. APF media 1 or APF media 2). The cells used in the vial thaw studies described in Example 1 were split into the same media (APF media 1 or APF media 2 supplemented with various concentrations of N-acetylcysteine) and allowed to recover in subsequent passages until a consistent doubling time from passage to passage was achieved. Viable cell density during exponential growth phase after recovery was used to calculate average cell doubling time as described in Example 1.

Figure 7:
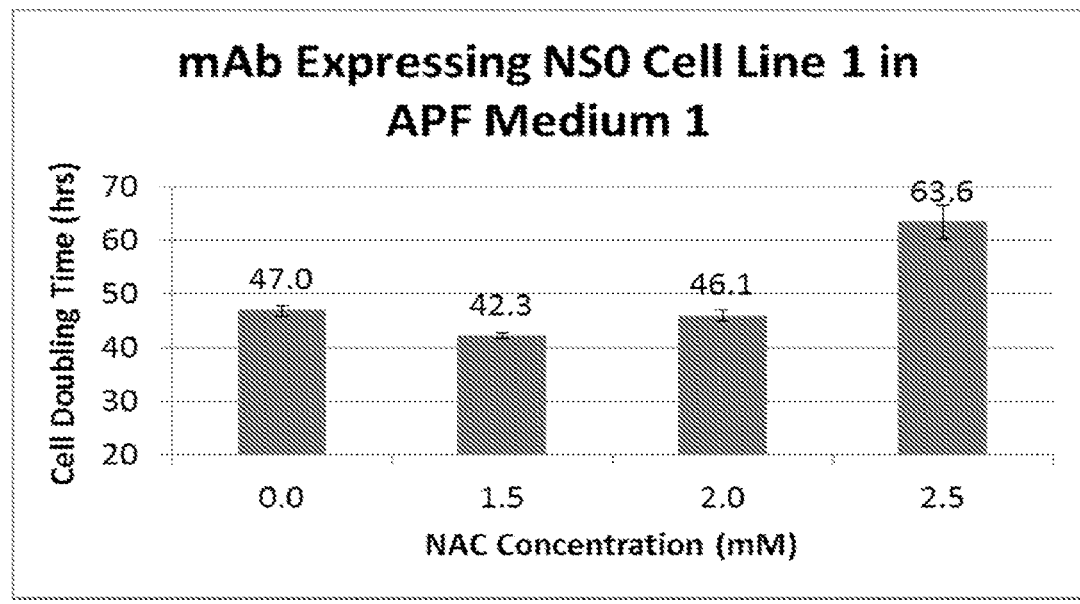
FIG. 7 shows population doubling time of NS0 Cell Line 1 expressing a monoclonal antibody ("mAb") against IL-9 in APF medium 1 during expansion. NS0 Cell Line 1 cells were cultured in animal-protein free (APF) medium 1 supplemented with N-acetylcysteine (NAC) (1.5 mM, 2.0 mM or 2.5 mM) and viable cell density during exponential growth phase was used to calculate average doubling time. Addition of 1.5 mM to 2.0 mM NAC increased cell growth and reduced average cell doubling time of NS0 Cell Line 1. hrs=hours; mM=millimolar; error bars represent 1 standard deviation of average doubling time.

FIG. 7 and Table 2 show NS0 Cell Line 1 cell doubling time in control medium (APF media 1 without NAC) and APF media 1 supplemented with three increasing concentrations of N-acetylcysteine during cell expansion. Addition of 1.5 mM to 2.0 mM NAC (1.5 mM or 2.0 mM) reduced average cell doubling time during cell expansion compared to NS0 Cell Line 1 cells cultured in control medium. Error bars represent 1 standard deviation (1 S.D.) of average doubling time.

TABLE 2

Population Doubling Time of NS0 Cell Line 1 in APF Medium 1 During Expansion

| NAC Concentration (mM) | Average Doubling Time (hrs) | 1 S.D. (hrs) |
|---|---|---|
| 0.0 | 47.0 | 1.0 |
| 1.5 | 42.3 | 0.4 |
| 2.0 | 46.1 | 1.1 |
| 2.5 | 63.6 | 3.2 |

Figure 8:
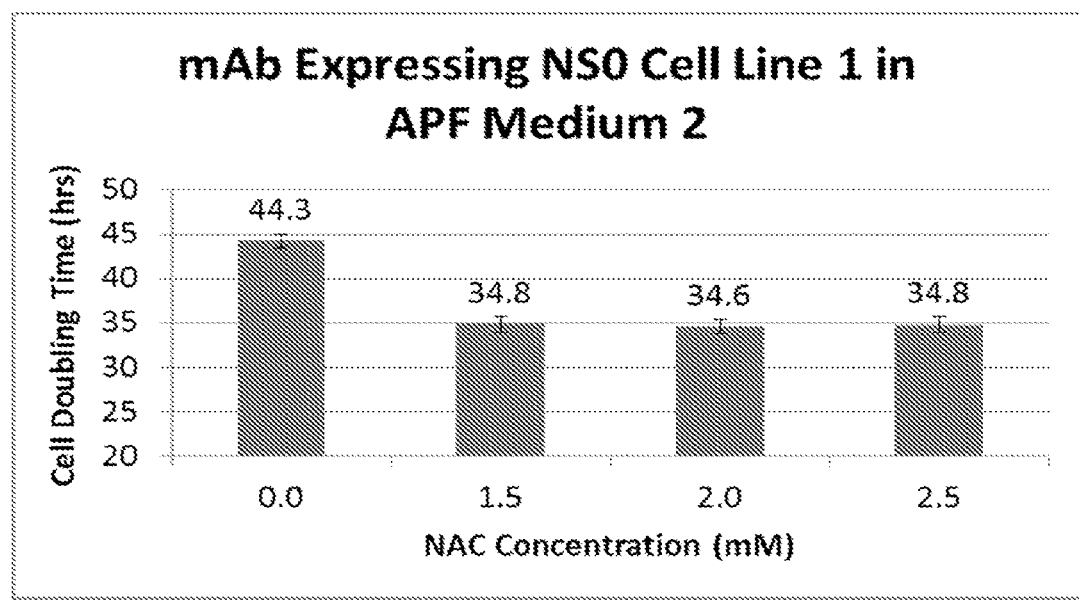
FIG. 8 shows population doubling time of NS0 Cell Line 1 expressing a monoclonal antibody ("mAb") against IL-9 in APF medium 2 during expansion. NS0 Cell Line 1 cells were cultured in animal-protein free (APF) medium 2 supplemented with various levels of N-acetylcysteine (NAC) (1.5 mM, 2.0 mM or 2.5 mM) and viable cell density during exponential growth phase was used to calculate average doubling time. Addition of 1.5 mM to 2.5 mM NAC increased cell growth and reduced average cell doubling time of NS0 Cell Line 1. hrs=hours; mM=millimolar; error bars represent 1 standard deviation of average doubling time.

FIG. 8 and Table 3 show NS0 Cell Line 1 cell doubling time in control medium (APF media 2 without NAC) and APF media 2 supplemented with three increasing concentrations of N-acetylcysteine during expansion. Similar to the results observed with APF media 1, addition of 1.5 mM to 2.5 mM NAC (1.5 mM, 2.0 mM or 2.5 mM NAC) reduced average cell doubling time during expansion compared to NS0 Cell Line 1 cells cultured in control medium. Error bars represent 1 standard deviation (1 S.D.) of average doubling time.

TABLE 3

Population Doubling Time of NS0 Cell Line 1 in APF Medium 2 During Expansion

| NAC Concentration (mM) | Average Doubling Time (hrs) | 1 S.D. (hrs) |
|---|---|---|
| 0.0 | 44.3 | 0.7 |
| 1.5 | 34.8 | 0.8 |
| 2.0 | 34.6 | 0.8 |
| 2.5 | 34.8 | 0.8 |

These experiments show that addition of N-acetylcysteine (about 1.5 mM to about 2.5 mM; or about 1.5 mM, about 2.0 mM or about 2.5 mM NAC) while NS0 cells are expanding increases cell viability, cell growth and reduces cell doubling time. In addition, N-acetylcysteine concentrations of 1.5 mM and 2.0 mM consistently increased cell viability, cell growth and reduced cell doubling time of NS0 cell line 1 cells undergoing cell expansion in two different media.

Example 5

Cell Doubling Time of NS0 Cell Line 2 in APF Medium 1, APF Medium 2 and CD Hybridoma Media During Cell Expansion NS0 cells (i.e. NS0 Cell Line 2) expressing a monoclonal antibody (i.e. BAK502G9, an anti-IL-13 antibody) were cultured in animal-protein free (APF) medium (i.e. APF media 1, APF media 2 or CD Hybridoma medium (Gibco) supplemented with cholesterol (1× Invitrogen Cholesterol Lipid Concentrate)). The cells used in the vial thaw studies described in Example 2 were split into the same media (APF media 1, APF media 2 or CD Hybridoma medium+cholesterol) supplemented with various concentrations of N-acetylcysteine and allowed to recover in subsequent passages until a consistent doubling time from passage to passage was achieved. Viable cell density during exponential growth phase after recovery was used to calculate average cell doubling time as described in Example 1.

Figure 9:
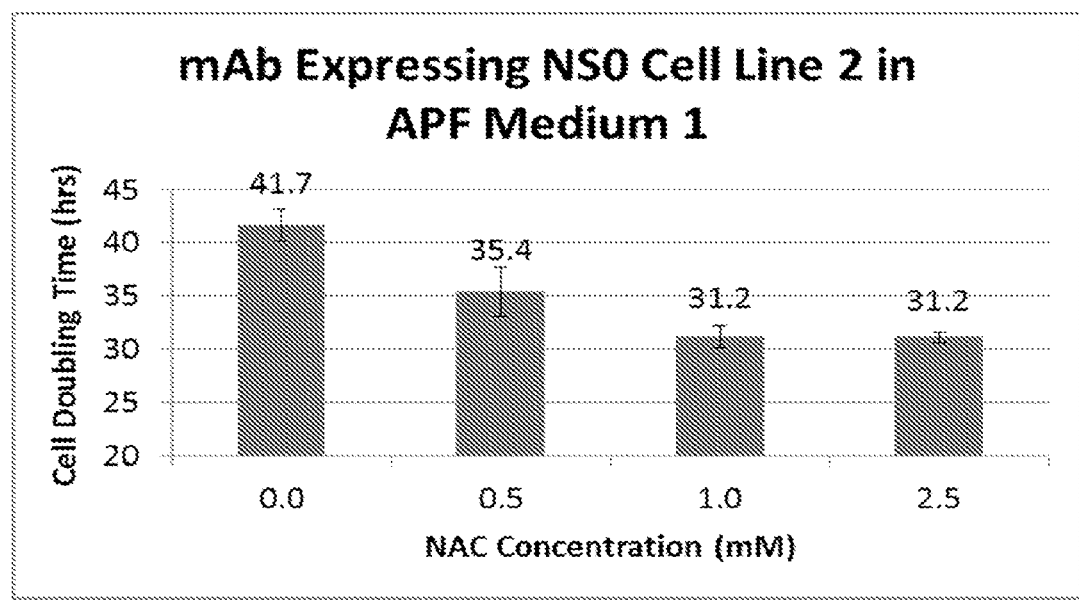
FIG. 9 shows population doubling time of NS0 Cell Line 2 expressing a monoclonal antibody ("mAb") against IL-13 in APF medium 1 during expansion. NS0 Cell Line 2 cells were cultured in animal-protein free (APF) medium 1 supplemented with N-acetylcysteine (NAC) (0.5 mM, 1.0 mM or 2.5 mM) and viable cell density during exponential growth phase was used to calculate average doubling time. Addition of 0.5 mM to 2.5 mM NAC increased cell growth and reduced average cell doubling time of NS0 Cell Line 2. hrs=hours; mM=millimolar; error bars represent 1 standard deviation of average doubling time.

FIG. 9 and Table 4 show NS0 Cell Line 2 cell doubling time in control medium (APF media 1 without NAC) and APF media 1 supplemented with three increasing concentrations of N-acetylcysteine during expansion. Addition of 0.5 mM to 2.5 mM NAC (0.5 mM, 1.0 mM or 2.5 mM) reduced average cell doubling time during expansion compared to NS0 Cell Line 2 cells cultured in control medium, with 1.0 mM and 2.5 mM NAC showing the greatest reduction of cell doubling time during expansion. Error bars represent 1 standard deviation (1 S.D.) of average doubling time.

TABLE 4

Population Doubling Time of NS0 Cell Line 2 in APF Medium 1 During Expansion

| NAC Concentration (mM) | Average Doubling Time (hrs) | 1 S.D. (hrs) |
| --- | --- | --- |
| 0.0 | 41.7 | 1.5 |
| 0.5 | 35.4 | 2.3 |
| 1.0 | 31.2 | 1.0 |
| 2.5 | 31.2 | 0.5 |

Figure 10:
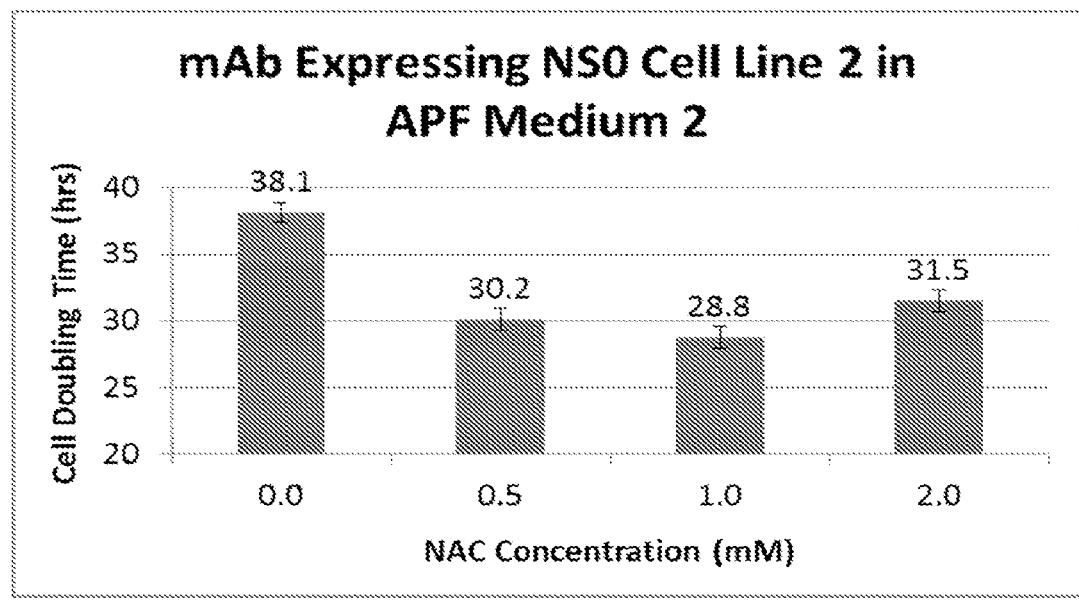
FIG. 10 shows population doubling time of NS0 Cell Line 2 expressing a monoclonal antibody ("mAb") against IL-13 in APF medium 2 during expansion. NS0 Cell Line 2 cells were cultured in animal-protein free (APF) medium 2 supplemented with N-acetylcysteine (NAC) (0.5 mM, 1.0 mM or 2.0 mM) and viable cell density during exponential growth phase was used to calculate average doubling time. Addition of 0.5 mM to 2.0 mM NAC increased cell growth and reduced average cell doubling time of NS0 Cell Line 2. hrs=hours; mM=millimolar; error bars represent 1 standard deviation of average doubling time.

FIG. 10 and Table 5 show NS0 Cell Line 2 cell doubling time in control medium (APF media 2 without NAC) and APF media 2 supplemented with three increasing concentrations of N-acetylcysteine during expansion. Similar to the results observed with APF media 1, addition of 0.5 mM to 2.0 mM NAC (0.5 mM, 1.0 mM, or 2.0 mM) reduced average cell doubling time during expansion compared to NS0 Cell Line 2 cells cultured in control medium. Error bars represent 1 standard deviation (1 S.D.) of average doubling time.

TABLE 5

Population Doubling Time of NS0 Cell Line 2 in APF Medium 2 During Expansion

| NAC Concentration (mM) | Average Doubling Time (hrs) | 1 S.D. (hrs) |
| --- | --- | --- |
| 0.0 | 38.1 | 1.2 |
| 0.5 | 30.2 | 0.2 |
| 1.0 | 28.8 | 0.6 |
| 2.0 | 31.5 | 0.2 |

Figure 11:
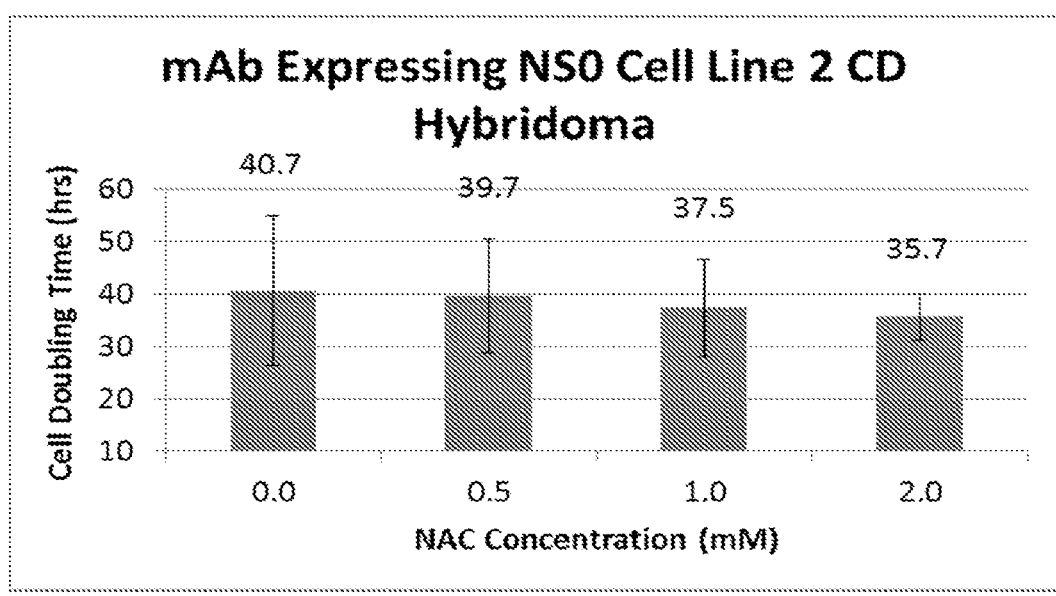
FIG. 11 illustrates population doubling time of NS0 Cell Line 2 expressing a monoclonal antibody against IL-13 in commercially available NS0 cell culture media (CD Hybridoma, Gibco) supplemented with cholesterol (1× Invitrogen Cholesterol Lipid Concentrate) during expansion. NS0 Cell Line 2 cells were cultured in CD Hybridoma medium with 1× Cholesterol Lipid Concentrate supplemented with N-acetylcysteine (NAC) (0.5 mM, 1.0 mM or 2.0 mM) and viable cell density during exponential growth phase was used to calculate average doubling time. Addition of 1.0 mM to 2.0 mM NAC increased cell growth and reduced average cell doubling time of NS0 Cell Line 2. Reduction of error bars also demonstrates that the cell growth is more robust. hrs=hours; mM=millimolar; error bars represent 1 standard deviation of average doubling time.

FIG. 11 and Table 6 show NS0 Cell Line 2 cell doubling time in control medium (CD Hybridoma medium (Gibco) supplemented with 1× Invitrogen Cholesterol Lipid Concentrate without NAC) and control medium containing three increasing concentrations of N-acetylcysteine during cell expansion. Similar to the results observed with APF media 1 and APF media 2, addition of 1.0 mM to 2.0 mM NAC reduced average cell doubling time compared to NS0 Cell Line 2 cells cultured in control medium. Error bars represent 1 standard deviation (1 S.D.) of average doubling time.

TABLE 6

Population Doubling Time of NS0 Cell Line 2 in Invitrogen CD Hybridoma Medium Supplemented with Cholesterol During Expansion

| NAC Concentration (mM) | Average Doubling Time (hrs) | 1 S.D. (hrs) |
| --- | --- | --- |
| 0.0 | 40.7 | 14.3 |
| 0.5 | 39.7 | 11.0 |
| 1.0 | 37.5 | 9.3 |
| 2.0 | 35.7 | 4.3 |

These experiments show that addition of N-acetylcysteine (about 0.5 mM to about 2.5 mM; or about 0.5 mM, about 1.0 mM, about 2.0 mM or about 2.5 mM NAC) to the cell culture media of NS0 cells during expansion increases cell viability, cell growth and reduces cell doubling time.

Example 6

Cell Doubling Time of NS0 Null Cell Line in APF Medium 2 During Cell Expansion

NS0 cells (i.e. NS0 Null Cell Line) not transfected with a heterologous protein were cultured in animal-protein free (APF) medium (i.e. APF media 2). The cells used in the vial thaw studies described in Example 3 were split into the same media (APF media 2 supplemented with various concentrations of N-acetylcysteine) and allowed to recover in subsequent passages until a consistent doubling time from passage to passage was achieved. Viable cell density during exponential growth phase after recovery was used to calculate average cell doubling time as described in Example 1.

Figure 12:
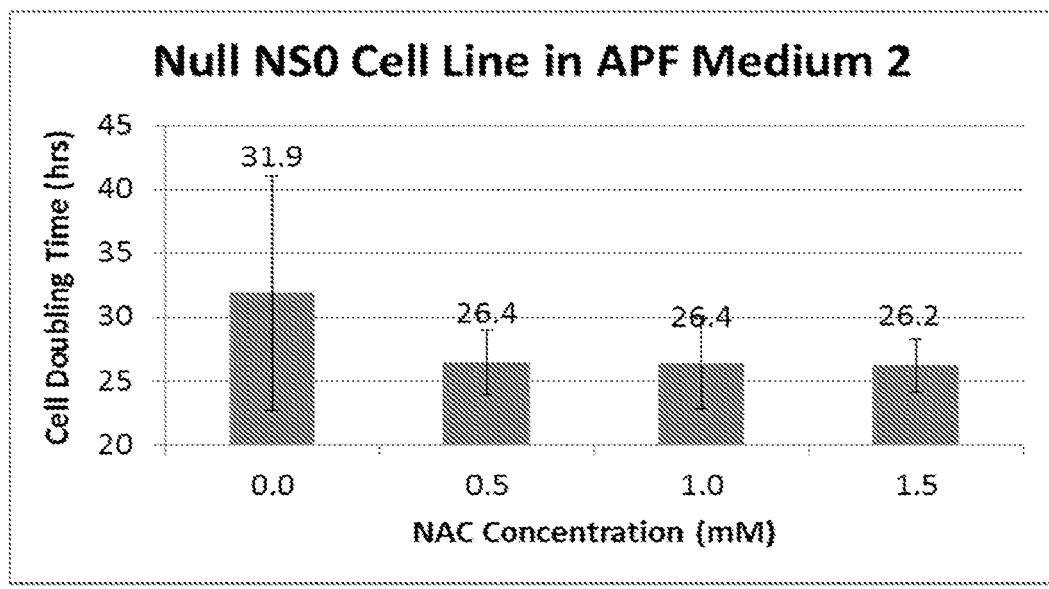
FIG. 12 shows population doubling time of an NS0 null cell line (an untransfected NS0 cell line not expressing a recombinant protein) in APF medium 2 during expansion. NS0 Null Cell Line cells were cultured in animal-protein free (APF) medium 2 supplemented with N-acetylcysteine (NAC) (0.5 mM, 1.0 mM or 1.5 mM) and viable cell density during exponential growth phase was used to calculate the average doubling time. Addition of 0.5 mM to 1.5 mM NAC increased cell growth and reduced average cell doubling time of the NS0 Null Cell Line. hrs=hours; mM=millimolar; error bars represent 1 standard deviation of average doubling time.

FIG. 12 and Table 7 show NS0 Null Cell Line cell doubling time in control medium (APF medium 2 without NAC) and APF media 2 supplemented with three increasing concentrations of N-acetylcysteine during expansion. Addition of 0.5 mM to 1.5 mM NAC (0.5 mM. 1.0 mM or 1.5 mM NAC) reduced cell doubling time during expansion compared to Null Cell Line cells cultured in control medium. Error bars represent 1 standard deviation (1 S.D.) of average doubling time.

These results, when taken together with the results summarized in Examples 4 and 5, show that three NS0 cell lines cultured in three different NS0 media supplemented with N-acetylcysteine at concentrations of 0.5 mM, 1.0 mM, 1.5 mM, and 2.0 mM (e.g. about 0.5 mM to about 2.0 mM) consistently had increased cell viability, cell growth and reduced cell doubling time of cells during cell expansion compared to NS0 cells thawed in control media.

TABLE 7

Population Doubling Time of NS0 Null Cell Line in APF Medium 2 During Expansion

| NAC Concentration (mM) | Average Doubling Time (hrs) | 1 S.D. (hrs) |
| --- | --- | --- |
| 0.0 | 31.9 | 9.2 |
| 0.5 | 26.4 | 2.5 |
| 1.0 | 26.4 | 3.6 |
| 1.5 | 26.2 | 2.1 |

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiments may be practiced in many ways and the claims include any equivalents thereof.

As used herein, the term about refers to a numeric value, including, for example, whole numbers, fractions, and percentages, whether or not explicitly indicated. The term about generally refers to a range of numerical values (e.g., +/−5% of the recited value) that one of ordinary skill in the art would consider equivalent to the recited value (e.g., having the same function or result). In some instances, the term about may include numerical values that are rounded to the nearest significant figure.

All publications, patents, patent applications, and/or other documents cited in this application are incorporated by reference in their entirety for all purposes to the same extent as if each individual publication, patent, patent application, and/or other document were individually indicated to be incorporated by reference for all purpose

What is claimed is:

1. A method of increasing cell viability, increasing cell growth rate or reducing cell doubling time comprising:
   a. providing a cell culture medium sufficient to support cell growth, wherein the cell culture medium comprises N-acetylcysteine; and
   b. culturing a cell in the cell culture medium, wherein the cell is an NS0 cell, wherein the N-acetylcysteine is at a concentration of from 0.25 mM to 3 mM.

2. The method of claim 1, wherein the cell culture medium is a serum free and animal-protein free medium or is a chemically-defined medium.

3. The method of claim 1, wherein the average doubling time of the cell is shorter than the average doubling time of a cell in a cell culture with a control medium without N-acetylcysteine, or the average doubling time of the cell is reduced by at least 10%, 15%, 20%, 25% or 50% compared to the control medium without N-acetylcysteine.

4. The method of claim 3, wherein the average cell doubling time is 60, 42, 32, 30 or 29 hours or less.

5. The method of claim 1, wherein the cell viability is increased over a cell culture with a control medium excluding N-acetylcysteine, or is increased by at least 5%, 7% or 10% compared to a cell culture medium without N-acetylcysteine, or wherein cell viability is at least 90%, 92% or 93%.

6. The method of claim 1, wherein the cells express a heterologous protein selected from the group consisting of:
   (a) an IL-13 antibody or antigen-binding fragment thereof;
   (b) an IL-13 antibody BAK502G9 or an antigen-binding fragment thereof;
   (c) an antibody or antigen binding fragment having a heavy chain variable region according to one of SEQ ID NOs: 1, 9, 17, or 25 and a light chain variable region according to one of SEQ ID NOs: 2, 10, 18, or 26; and
   (d) an antibody or antigen binding fragment comprising: a heavy chain variable region and a light chain variable region, comprising:
      i. a HC CDR1 according to SEQ ID NO: 3, an HC CDR2 according to SEQ ID NO: 4, an HC CDR3 according to SEQ ID NO: 5, an LC CDR1 according to SEQ ID NO: 6, an LC CDR2 according to SEQ ID NO: 7, and an LC CDR3 according SEQ ID NO: 8;
      ii. a HC CDR1 according to SEQ ID NO: 11, an HC CDR2 according to SEQ ID NO: 12, an HC CDR3 according to SEQ ID NO: 13, an LC CDR1 according to SEQ ID NO: 14, an LC CDR2 according to SEQ ID NO: 15, and an LC CDR3 according SEQ ID NO: 16;
      iii. a HC CDR1 according to SEQ ID NO: 19, an HC CDR2 according to SEQ ID NO: 20, an HC CDR3 according to SEQ ID NO: 21, an LC CDR1 according to SEQ ID NO: 22, an LC CDR2 according to SEQ ID NO: 23, and an LC CDR3 according SEQ ID NO: 24; or
      iv. a HC CDR1 according to SEQ ID NO: 27, an HC CDR2 according to SEQ ID NO: 28, an HC CDR3 according to SEQ ID NO: 29, an LC CDR1 according to SEQ ID NO: 30, an LC CDR2 according to SEQ ID NO: 31, and an LC CDR3 according SEQ ID NO: 32.

* * * * *